United States Patent
Prusiner et al.

(10) Patent No.: US 6,372,214 B1
(45) Date of Patent: *Apr. 16, 2002

(54) ANTIBODIES SPECIFIC FOR NATIVE PRP$^{Sc}$

(75) Inventors: Stanley B. Prusiner, San Francisco; R. Anthony Williamson, San Diego; Dennis R. Burton, La Jolla, all of CA (US)

(73) Assignees: The Regents of the University of California, Oakland; The Scripps Research Institute, La Jolla, both of CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/550,374

(22) Filed: Apr. 13, 2000

Related U.S. Application Data

(63) Continuation of application No. 09/036,579, filed on Mar. 6, 1998, which is a division of application No. 08/713,939, filed on Sep. 13, 1996, now Pat. No. 5,846,533, which is a continuation-in-part of application No. 08/528,104, filed on Sep. 14, 1995, now abandoned.

(51) Int. Cl.$^7$ ...................... A61K 39/395; C12P 19/00; G01N 33/567; G01N 33/543; C07K 16/00
(52) U.S. Cl. ................. 424/130.1; 424/9.1; 424/147.1; 435/7.1; 435/70.1; 435/71.1; 436/503; 436/518; 436/547; 530/387.1
(58) Field of Search ............................. 424/9.1, 130.1, 424/147.1; 435/7.1, 70.1, 71.1; 530/387.1; 436/518, 503, 547

(56) References Cited

U.S. PATENT DOCUMENTS

| | | |
|---|---|---|
| 4,806,627 A | 2/1989 | Wisniewski et al. |
| 4,816,567 A | 3/1989 | Cabilly et al. |
| 5,223,409 A | 6/1993 | Ladner et al. |

FOREIGN PATENT DOCUMENTS

| | | |
|---|---|---|
| WO | WO 90/04036 | 4/1990 |
| WO | WO 93/10227 | 5/1995 |

OTHER PUBLICATIONS

Barbas et al., "Assembly of Combinatorial Antibody Libraries on Phage Surfaces: the Gene III Site," *Proc. Natl. Acad. Sci.* (1991) 88: 7978–82.
Barry, R.A., et al., "Monoclonal Antibodies to the Cellular and Scrapie Prion Proteins," *Journal of Infectious Diseases* (1986) 154:518–521.
Basler et al., "Scrapie and Cellular PrP Isoforms Are Encoded by the Same Chromosomal Gene," *Cell*, (1986) 46: 417–28.
Bendheim et al., "Scrapie and Creutzfeldt–Jacob Disease Prion Proteins Share Physical Properties and Antigenic Determinants," *Proc. Natl. Acad. Sci. USA* (1985) 82:997–1001.
Bobrzecka et al., "The Method of Controlled Rearrangement of Protein Disulphides and Its Use for Synthesis of Chimeric Immunoglobulin G," *Immunology Letters* (1980) 2: 151–5.
Bode et al., "Characterization of Antisera Against Scrapie–Associated Fibrils (SAF) from Affected Hamster and Cross–Reactivity with SAF from Scrapie–Affected Mice and from Patients with Creutzfeldt–Jacob Disease," *J. Gen. Virol.* (1985) 66(pt 11):2471–8.
Bolton et al., "Identification of a Protein That Purifies with the Scrapie Prion," *Science* (1982) 218: 1309–11.
Brown et al., "Diagnosis of Creutzfeldt–Jacob disease by western blot identification of marker protein in human brain tissue," *New Engl. J. Med.* (1986) 314:547–51.
Brown et al., "Friendly Fire' in Medicine: Hormones, Homografts, and Creutzfeldt–Jakob Disease," *Lancet* (1992) 340: 24–27.
Bruce, et al., "Biological Evidence that Scrapie Agent Has an Idependent Genome," *J. Gen. Virol.* (1987) 68:79–89.
Buchanan et al., "Mortality, Neoplasia, and Creutzfeldt–Jakob Disease in Patients Treated with Human Pituitary Growth Hormone in the United Kingdom", *BMJ* (1991) 302:824–828.
Bucchine et al., "Rearrangement of a chicken Immunoglobulin Gene Occurs in the Lymphoid Lineage of a Transgenic Mouse," *Nature* (1987) 326: 409–11.
Bueler et al., "Mice Devoid of PrP are Resistant to Scrapie," *Cell* (1993) 73:1339–1347.
Bueler et al., "Normal Development and Behavior of Mice Lacking the Neuronal Cell–surface PrP Protein," *Nature* (1992) 356:577–582.

(List continued on next page.)

*Primary Examiner*—Rodney P Swartz
(74) *Attorney, Agent, or Firm*—Karl Bozicevic; Bozicevic, Field & Francis LLP

(57) ABSTRACT

Antibodies are disclosed which specifically bind to native PrP$^{Sc}$ in situ. Preferred antibodies bind only to the native PrP$^{Sc}$ of a particular species e.g., human, cow, sheep, pig, etc. Particularly preferred antibodies bind specifically to a particular isoform of human PrP$^{Sc}$. Preferred antibodies of the invention are (1) produced by phage display methodology, (2) bind specifically to native PrP$^{Sc}$, (3) neutralizes the infectivity of prions, (4) bind to PrP$^{Sc}$ in situ and (5) bind 50% or more of PrP$^{Sc}$ in a liquid flowable sample. Antibodies of the invention can be bound to a substrate and used to assay a sample (which has any PrP$^{Sc}$ denatured via proteinase K) for the presence of PrP$^{Sc}$ of a specific species which PrP$^{Sc}$ is associated with disease. Antibodies which specifically bind to human PrP$^{Sc}$ can be labeled and injected carrying out an in vivo diagnostic test to determine if the human is infected with prions associated with disease. The antibodies are preferably produced using phage display technology wherein the genetic material in the phage expressing the antibody is obtained from a mammal with an ablated endogenous PrP protein gene and an endogenous chimeric PrP gene which mammal had been inoculated with PrP$^{Sc}$ to induce antibody production.

12 Claims, 12 Drawing Sheets

OTHER PUBLICATIONS

Burton, D.R. et al., "A Large Array of Human Monoclonal Antibodies to Type 1 Human Immunodeficiency Virus from Combinatorial Libraries of Asymptomatic Seropositive Individuals," *Proc. Natl. Acad. Sci. USA* (1991) 88: 10134–7.

Burton and Barbas, "Human Antibodies from Combinatorial Libraries," *Adv. Immunol.* (1994) 57: 191–280.

Cann et al., "Antibody fragments to PrP generated using phage display technology," *J. Cell. Bichem. Supplement* (1994) 18D:T304.

Carlson, G.A., et al., "Prion Isolate Specified Allotypic Interactions Between the Cellular and Scrapie Prion Potiens in Congenic and Transgenic Mice," *Proc. Natl. Acad. Sci. USA* (1994) 91:5690–4.

Clackson, T., et al., "Making Antibody Fragments Using Phage Display Libraries," *Nature* (1991) 352: 624–8.

Cochius et al., "Creutzfeldt–Jakob Disease in a Recipient of Human Pituitary–Derived Gonadotrophin: A Second Case," *J. Neurol. Neurosurg. Psychiatry* (1992) 55:1094–1095.

Cochius et al., "Creutzfeldt–Jakob Disease in a Recipient of Human Pituitary–Derived Gonadotrophin," *Aust. N.Z. J. Med.* (1990) 20:592–593.

Collinge et al., "Genetic Predisposition to Latrogenic Creutzfeldt–Jakob Disease," *Lancet* (1991) 337:1441–1442.

Ditzel, J., et al., "Neutralizing Recombinany Human Antibodies to a Conformational V2– and CD4–biding Site–Sensitive Epitope of HIV-1 gp120 Isolated by Using an Epitope–Masking Procedure." *J. Immunol.* (1995) 154: 893–906.

Gabizon et al., "Immunoaffinity purification and neutralization of scrapie prion infectivity," *Proc. Natl. Acad. Sci. USA* (1988) 85:6617–6621.

Gabriel et al., "Molecular Cloning of a Candidate Chicken Prion Protein," *Proc. Natl. Acad. Sci. USA* (1992) 89:9097–9101.

Gajdusek, D.C., "Unconventional Viruses and the Origin and Disappearance of Kuru," *Science* (1977) 197:943–960.

Gibbs, Jr. et al., "Creutzfeldt–Jakob Disease Infectivity of Growth Hormone Derived from Human Pituitary Glands," *N. Engl. J. Med.* (1993) 328:358–359.

Goldfarb et al., "Fatal Familial Insomnia and Familial Creutzfeldt–Jakob Disease: Disease Phenotype Determined by a DNA Polymorphism," *Science* (1992) 258:806–808.

Goldmann et al., "Two Alleles of a Neural Protein Gene Linked to Scrapie in Sheep," *Proc. Natl. Acad. Sci. USA* (1990) 87:2476:2480.

Goldman et al., "Different Forms of the Bovine PrP Gene Have Five or Six Copies of a Short, G–C Rich Element within the protein–coding Exon," *J. Gen. Virol.* (1991) 72:201–204.

Goodhardt, et al., "Rearrangement and Expression of Rabbit Immunoglobulin k Light Chain Gene in Transgenic Mice," *Proc. Natl. Acad. Sci. USA* (1987) 84: 4229–33.

Harris et al., "A Prion–like Protein from Chicken Brain Copurifies with an Acetylcholine Receptor–Inducing Activity," *Proc. Natl. Acad. Sci. USA* (1991) 88:7664–7668.

Healy et al., "Creutzfeldt–Jakob Disease After Pituitary Gonadotrophin: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Horiuchi, "Interaction between Gene II Protein and the DNA Replication Origin of Bacteriophage f1," *J. Mol. Biol.*, (1986) 188:215–223.

Hsaio et al., "Linkage of a Prion Protein Missense Variant to Gertsmann–Straussler Syndrome," *Nature* (1989) 383:342–345.

Hsaio et al., "A Prion Protein Variant in a Family with the a Telencephalic Form of Gertsmann–Strussler–Scheinker Syndrome," *Neurology*(1991) 41:681–684.

Huse et al., "Generation of a Large Combinatorial Library of the Immunoglobulin Repertoire in Phage Lambda (see comments)," *Science* (1989) 246: 1275–81.

Kascsak, R.J., et al., "Mouse Polyclonal and Monoclonal Antibody to Scrapie–Associated Fibril Proteins" *Journal of Virology* (1987) 61:3688–3693.

Kellings et al., "Further Analysis of Nucleic Acids in Purified Scrapie Prion Preparations by Improved Return Refocusing Gel Electrophoresis," *J. Gen Virol.* (1992) 73: 1025–29.

Koch et al., "Creutzfeldt–Jakob Disease in a Young Adult with Idiopathic Hypopituitarism," *N. Engl. J. Med.* (1985) 313:731–733.

Konieczny et al., "The Combination of IgM Subunits and Proteolytic IgG Fragment by Controlled Formaion of Interchain Disulphides." *Haematologia* (1981) 14(1): 85–91.

Kretzschmar et al., "Molecular Cloning of a Human Prion Protein cDNA," *DNA* (1986) 5:315–324.

Kretzchmar et al., "Molecular Cloning of a Mink Prion Gene," *J. Gene Virol.* (1992) 73:2757–2761.

Lasmezas et al., "Recombinant Human Growth Hormone and Insulin–Like Growth Factor I Induce PRP Gene Expression in PC12 Cell," *Biochem. Biophys. Res. Commun.* (1993) 196:1163–1169.

Locht et al., "Molecular Cloning and Complete Sequence of Prion Protein cDNA from Mouse Brain Infected with the Scrapie Agent," *Proc. Natl. Acad. Sci USA* (1986) 83:6372–6376.

McKinley et al., "A Protease–Resistant Protein is a Structural Component of the Scrapie Prion," *Cell* (1983) 35:57–62.

Medori et al., "Fatal Familial Insomnia, a Prion Disease with a Mutation at Codon 178 of the Prion Protein Gene," *N. Engl. J. Med* (1992) 326:444–449.

Melhorn et al., "High–Level Expression and Characterization of a Purified 142–residue Polypeptide of the Prion Protein," *Biochemistry* (1996) 35:5528–2237.

Meyer et al., "Separation and Properties of Cellular and Scrapie Prion Proteins," *Proc. Natl. Acad. Sci. USA* (1986) 83: 3693–7.

Meyer et al., "Search for a Putative Scrapie Genome in Purified Prion Fractions Reveals a Paucity of Nucleic Acids," *J. Gen. Virol.* (1991) 72 (Pt.1) :37–49.

Nisbet et al., "Creutzfeldt–Jakob Disease in a Second Patient Who Received a Cadaveric Dura mater Graft," *J.Am.Med.Assoc.* (1989) 216:1118.

Oesch, et al., "A Cellular Gene Encodes a Scrapie PrP 27–30 Protein," *Cell* (1985) 40: 735–46.

Ohkawa et al., "The Orientation of the Major Coat Protein of Bacteriophage f1 in the Cytoplasmic Membrane of *Escherichia coli*\*" *Journal of Biological Chemistry* (1981) 256:9951–9958.

Patel, "Placenta Donors to be Screened for Brian Disease," *New Scientist*, Nov. 20, 1993, p. 10.

Prusiner et al., "Ablation of the Prion Protein (PrP) Gene in Mice Prevents Scrapie and Facilitates Production of Anti--PrP Antibodies," *Proc. Natl. Acad. Sci. USA* (1993) 90:10608–10612.

Prusiner et al., "Molecular Biology of Prion Dieases," *Science* (1991) 252:1515–1522.

Prusiner, S.B., et al., "Scrapie prions aggregate to form amyloid–like birefringent rods," *Cell* 1983 35: 349–58.

Prusiner et al., "Further Purification and Characterization of Scrapie Prions," *Biochemistry* (1982) 21:6942–50.

Rasched, et al., "Ff Coliphages: Structural and Functional Relationships," *Microbiological Reviews* (1986) 50:401–427.

Rogers et al., "Epitope Mapping of the Syrian Hamster Prion Protein Using Chimeric and Mutant Genes in a Vaccinia Virus Expression System,"*J. Immunol.* 1991. 147: 3568–74.

Scott et al., "Propagation of Prions with Artificial Properties in Transgenic Mice Expressing Chimeric PrP Genes," *Cell* (1993) 73:979–988.

Scott, M., et al., "Transgenic Mice Expressing Hamster Prion Protein Produce Species Specific Infectivity and Amyloid Plaques," *Cell* (1989) 59:847–57.

Serban et al, "Rapid Detection of Creuzfeldt–Jakob Disease and Scrapie Prion Proteins," *Neurology* (1990) 40:110–7.

Short, et al., "λ ZAP: a bacteriophage λ expression vector with in vivo excision properties," *Nucleic Acids Research* (1988) 16:7583–7600.

Stahl et al., "Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi et al., "Transmission of Chronic Spongiform Encephalopathy with Kuru Plaques from Humans to Small Rodents," *Ann.Neurol.* (1979) 5:581–584.

Thadani et al., "Creutzfeldt–Jakob Disease Probably Acquired From a Cadaveric Dura Mater Graft," *J. Neurosurg.* (1988) 69:766–769.

Westaway et al., Homozygosity for Prion Alleles Encoding Glutamine–171 Renders Sheep Susceptible to Natural Scrapie,: *Genes Dev.* (1994) 8:959–969.

Williamson, R.A., et al., "Human Monoclonal Antibodies Against a Plethora of Viral Pathogens from Single Combinatorial Libraries," *Proc. Natl. Acad. Sci. USA* (1993) 90:4141–5.

Willison et al., "Creutzfeldt–Jakob Disease Following Cadaveric Dura Mater Graft," *Neurosurg. Psychiatric* (1991) 54:940.

Gabizon et al., "Immunoaffinity purification and neutralization of scrapie prion infectivity," *Proc Natl Acad Sci USA*, 85:6617–6621 (Sep. 1988).

| | | | | | | | | | | | | | | | | |
|---|---|---|---|---|---|---|---|---|---|---|---|---|---|---|---|---|
| Mo | Met | Ala | Asn | Leu | Gly | Tyr | Trp | Leu | Leu | Ala | Leu | Phe | Val | Thr | Met | Trp | 16 |
| Hu | | | | | | | Cys | | Met | | Val | | | | Ala | Thr | |
| Mo | Thr | Asp | Val | Gly | Leu | Cys | Lys | Lys | Arg | Pro | Lys | Pro | Gly | Gly | Trp | Asn | 32 |
| Hu | Ser | | Leu | | | | | | | | | | | | | | |
| Mo | Thr | Gly | Gly | Ser | Arg | Tyr | Pro | Gly | Gln | Gly | Ser | Pro | Gly | Gly | Asn | Arg | 48 |
| Hu | | | | | | | | | | | | | | | | | |
| Mo | Tyr | Pro | Pro | Gln | Gly | Gly | - - - | Thr | Trp | Gly | Gln | Pro | His | Gly | Gly | Gly | 63 |
| Hu | | | | | | | Gly | Gly | | | | | | | | | |
| Mo | Trp | Gly | Gln | Pro | His | Gly | Gly | Ser | Trp | Gly | Gln | Pro | His | Gly | Gly | Ser | 79 |
| Hu | | | | | | | | Gly | | | | | | | | Gly | |
| Mo | Trp | Gly | Gln | Pro | His | Gly | Gly | Gly | Trp | Gly | Gln | Gly | Gly | Gly | Thr | His | 95 |
| Hu | | | | | | | | | | | | | | | | | |
| Mo | Asn | Gln | Trp | Asn | Lys | Pro | Ser | Lys | Pro | Lys | Thr | Asn | Leu | Lys | His | Val | 111 |
| Hu | Ser | | | | | | | | | | | | Met | | Met | | |
| Mo | Ala | Gly | Ala | Ala | Ala | Ala | Gly | Ala | Val | Val | Gly | Gly | Leu | Gly | Gly | Tyr | 127 |
| Hu | | | | | | | | | | | | | | | | | |
| Mo | Met | Leu | Gly | Ser | Ala | Met | Ser | Arg | Pro | Met | Ile | His | Phe | Gly | Asn | Asp | 143 |
| Hu | | | | | | | | | | Ile | | | | | | Ser | |
| Mo | Trp | Glu | Asp | Arg | Tyr | Tyr | Arg | Glu | Asn | Met | Tyr | Arg | Tyr | Pro | Asn | Gln | 159 |
| Hu | Tyr | | | | | | | | | | | His | | | | | |
| Mo | Val | Tyr | Tyr | Arg | Pro | Val | Asp | Gln | Tyr | Ser | Asn | Gln | Asn | Asn | Phe | Val | 175 |
| Hu | | | | | | | Met | Glu | | | | | | | | | |
| Mo | His | Asp | Cys | Val | Asn | Ile | Thr | Ile | Lys | Gln | His | Thr | Val | Thr | Thr | Thr | 191 |
| Hu | | | | | | | | | | | | | | | | | |
| Mo | Thr | Lys | Gly | Glu | Asn | Phe | Thr | Glu | Thr | Asp | Val | Lys | Met | Met | Glu | Arg | 207 |
| Hu | | | | | | | | | | | | | | | | | |
| Mo | Val | Val | Glu | Gln | Met | Cys | Val | Thr | Gln | Tyr | Gln | Lys | Glu | Ser | Gln | Ala | 223 |
| Hu | | | | | | | Ile | | | | Glu | Arg | | | | | |
| Mo | Tyr | Tyr | Asp | Gly | Arg | Arg | Ser | Ser | Ser | Thr | Val | Leu | Phe | Ser | Ser | Pro | 239 |
| Hu | | | Gln | | - - - | - - - | | Gly | | Met | | | | | | | |
| Mo | Pro | Val | Ile | Leu | Leu | Ile | Ser | Phe | Leu | Ile | Phe | Leu | Ile | Val | Gly | | 254 |
| Hu | | | | | | | | | | | | | | | | | |

Predicted amino acid sequence of mouse PrP and the amino acid differences between mouse and human PrP.

(SEQ. ID NOS. 1 and 2)

FIG. 2

```
Mo  Met Ala Asn Leu ---  --- Gly Tyr Trp Leu Leu Ala Leu Phe Val Thr  14
Bo      Val Lys Ser His  Ile     Ser Ile     Val             Ala

Mo  Met Trp Thr Asp Val Gly Leu Cys Lys Lys Arg Pro Lys Pro Gly Gly  30
Bo          Ser

Mo  --- Trp Asn Thr Gly Gly Ser Arg Tyr Pro Gly Gln Gly Ser Pro Gly  45
Bo

Mo  Gly Asn Arg Tyr Pro Pro Gln Gly Gly --- Thr Trp Gly Gln Pro His  60
Bo                                  Gly Gly

Mo  Gly Gly Gly Trp Gly Gln Pro His Gly Gly Ser Trp Gly Gln Pro His  76
Bo                                          Gly

Mo  Gly Gly Ser Trp Gly Gln Pro His Gly Gly Gly Trp Gly Gln --- ---  90
Bo          Gly                                             Pro His

Mo  --- --- --- --- --- --- Gly Gly Gly Thr His Asn Gln Trp Asn Lys  100
Bo  Gly Gly Gly Gly Trp Gly Gln                 Gly

Mo  Pro Ser Lys Pro Lys Thr Asn Leu Lys His Val Ala Gly Ala Ala Ala  116
Bo                                  Met

Mo  Ala Gly Ala Val Val Gly Gly Leu Gly Gly Tyr Met Leu Gly Ser Ala  132
Bo

Mo  Met Ser Arg Pro Met Ile His Phe Gly Asn Asp Trp Glu Asp Arg Tyr  148
Bo              Leu                     Ser     Tyr

Mo  Tyr Arg Glu Asn Met Tyr Arg Tyr Pro Asn Gln Val Tyr Tyr Arg Pro  164
Bo                      His

Mo  Val Asp Gln Tyr Ser Asn Gln Asn Asn Phe Val His Asp Cys Val Asn  180
Bo

Mo  Ile Thr Ile Lys Gln His Thr Val Thr Thr Thr Thr Lys Gly Glu Asn  200
Bo          Val     Glu

Mo  Phe Thr Glu Thr Asp Val Lys Met Met Glu Arg Val Val Glu Gln Met  212
Bo                          Ile

Mo  Cys Val Thr Gln Tyr Gln Lys Glu Ser Gln Ala Tyr Tyr Asp Gly Arg  228
Bo                                                          Gln ---

Mo  Arg Ser Ser Ser Thr Val Leu Phe Ser Ser Pro Pro Val Ile Leu Leu  244
Bo      --- Gly Ala     Val Ile

Mo  Ile Ser Phe Leu Ile Phe Leu Ile Val Gly                          254
Bo
```

Predicted amino acid sequence of mouse PrP and the amino acid differences between mouse and bovine PrP.
(SEQ. ID NOS. 1 and 3)

FIG. 3

| | | | | | | | | | | | | | | | |
|---|---|---|---|---|---|---|---|---|---|---|---|---|---|---|---|
| Mo | Met | Ala | Asn | Leu | --- | --- | Gly | Tyr | Trp | Leu | Leu | Ala | Leu | Phe | Val | Thr | 14 |
| Sh | | Val | Lys | Ser | His | Ile | | | Ser | | Ile | | Val | | | Ala |

| | | | | | | | | | | | | | | | |
|---|---|---|---|---|---|---|---|---|---|---|---|---|---|---|---|
| Mo | Met | Trp | Thr | Asp | Val | Gly | Leu | Cys | Lys | Lys | Arg | Pro | Lys | Pro | Gly | Gly | 30 |
| Sh | | | Ser | | | | | | | | | | | | | |

| | | | | | | | | | | | | | | | |
|---|---|---|---|---|---|---|---|---|---|---|---|---|---|---|---|
| Mo | --- | Trp | Asn | Thr | Gly | Gly | Ser | Arg | Tyr | Pro | Gly | Gln | Gly | Ser | Pro | Gly | 45 |
| Sh | | | | | | | | | | | | | | | | |

| | | | | | | | | | | | | | | | |
|---|---|---|---|---|---|---|---|---|---|---|---|---|---|---|---|
| Mo | Gly | Asn | Arg | Tyr | Pro | Pro | Gln | Gly | Gly | --- | Thr | Trp | Gly | Gln | Pro | His | 60 |
| Sh | | | | | | | | | | Gly | Gly | | | | | |

| | | | | | | | | | | | | | | | |
|---|---|---|---|---|---|---|---|---|---|---|---|---|---|---|---|
| Mo | Gly | Gly | Gly | Trp | Gly | Gln | Pro | His | Gly | Gly | Ser | Trp | Gly | Gln | Pro | His | 76 |
| Sh | | | | | | | | | | | Gly | | | | | |

| | | | | | | | | | | | | | | | |
|---|---|---|---|---|---|---|---|---|---|---|---|---|---|---|---|
| Mo | Gly | Gly | Ser | Trp | Gly | Gln | Pro | His | Gly | Gly | Gly | --- | Trp | Gly | Gln | Gly | 91 |
| Sh | | | | | | | | | | | | Gly | | | | |

| | | | | | | | | | | | | | | | |
|---|---|---|---|---|---|---|---|---|---|---|---|---|---|---|---|
| Mo | Gly | Gly | Thr | His | Asn | Gln | Trp | Asn | Lys | Pro | Ser | Lys | Pro | Lys | Thr | Asn | 107 |
| Sh | | | Ser | --- | His | Ser | | | | | | | | | | |

| | | | | | | | | | | | | | | | |
|---|---|---|---|---|---|---|---|---|---|---|---|---|---|---|---|
| Mo | Leu | Lys | His | Val | Ala | Gly | Ala | Ala | Ala | Ala | Gly | Ala | Val | Val | Gly | Gly | 123 |
| Sh | Met | | | | | | | | | | | | | | | |

| | | | | | | | | | | | | | | | |
|---|---|---|---|---|---|---|---|---|---|---|---|---|---|---|---|
| Mo | Leu | Gly | Gly | Tyr | Met | Leu | Gly | Ser | Ala | Met | Ser | Arg | Pro | Met | Ile | His | 139 |
| Sh | | | | | | | | | | | | | | | Leu | |

| | | | | | | | | | | | | | | | |
|---|---|---|---|---|---|---|---|---|---|---|---|---|---|---|---|
| Mo | Phe | Gly | Asn | Asp | Trp | Glu | Asp | Arg | Tyr | Tyr | Arg | Glu | Asn | Met | Tyr | Arg | 155 |
| Sh | | | | | | Tyr | | | | | | | | | | |

| | | | | | | | | | | | | | | | |
|---|---|---|---|---|---|---|---|---|---|---|---|---|---|---|---|
| Mo | Tyr | Pro | Asn | Gln | Val | Tyr | Tyr | Arg | Pro | Val | Asp | Gln | Tyr | Ser | Asn | Gln | 171 |
| Sh | | | | | | | | | | | | | | | | |

| | | | | | | | | | | | | | | | |
|---|---|---|---|---|---|---|---|---|---|---|---|---|---|---|---|
| Mo | Asn | Asn | Phe | Val | His | Asp | Cys | Val | Asn | Ile | Thr | Ile | Lys | Gln | His | Thr | 187 |
| Sh | | | | | | | | | | | | Val | | | | |

| | | | | | | | | | | | | | | | |
|---|---|---|---|---|---|---|---|---|---|---|---|---|---|---|---|
| Mo | Val | Thr | Thr | Thr | Thr | Lys | Gly | Glu | Asn | Phe | Thr | Glu | Thr | Asp | Val | Lys | 203 |
| Sh | | | | | | | | | | | | | | | Ile | |

| | | | | | | | | | | | | | | | |
|---|---|---|---|---|---|---|---|---|---|---|---|---|---|---|---|
| Mo | Met | Met | Glu | Arg | Val | Val | Glu | Gln | Met | Cys | Val | Thr | Gln | Tyr | Gln | Lys | 219 |
| Sh | Ile | | | | | | | | | | | Ile | | | | Arg |

| | | | | | | | | | | | | | | | |
|---|---|---|---|---|---|---|---|---|---|---|---|---|---|---|---|
| Mo | Glu | Ser | Gln | Ala | Tyr | Tyr | Asp | Gly | Arg | Arg | Ser | Ser | Ser | Thr | Val | Leu | 235 |
| Sh | | | | | | | Gln | --- | --- | | Gly | Ala | | | Val | Ile |

| | | | | | | | | | | | | | | | |
|---|---|---|---|---|---|---|---|---|---|---|---|---|---|---|---|
| Mo | Phe | Ser | Ser | Pro | Pro | Val | Ile | Leu | Leu | Ile | Ser | Phe | Leu | Ile | Phe | Leu | 251 |
| Sh | | | | | | | | | | | | | | | | |

| | | | |
|---|---|---|---|
| Mo | Ile | Val | Gly | 254 |
| Sh | | | | |

Predicted amino acid sequence of mouse PrP and the amino acid differences between mouse and sheep PrP.

(SEQ. ID NOS. 1 and 4)  FIG. 4

| | FR1 | CDR1 | FR2 |
|---|---|---|---|
| PrP 28 (SEQ. ID NOS. 68 and 69) | LEQSGVELARPGASVMLSCKASGYTFT | TYGIS | WVKQRTGQGLEWIG |
| PrP 81 (SEQ. ID NOS. 70) | YTFT | TYGIT | WVKQRTGQGLEWIG |
| PrP 37 (SEQ. ID NOS. 71) | XTFT | VYGIS | WVKQRTGQGLEWIG |

B

| | FR1 | CDR1 | FR2 |
|---|---|---|---|
| PrP 81 (SEQ. ID NOS. 72) | WEXRVSLTC | RASQDFGSSLN | WFRQKPDGTIRRLIY |
| PrP 28 (SEQ. ID NOS. 73) | ELVMTQTPSSLSASLGERVSLTC | RASQDFGSSLN | WFRQAPDGTIRRLIY |
| PrP 37 (SEQ. ID NOS. 74) | ELQMTQTPSSLSVSLGERVSLTC | RASQDIGSSLN | WLQQEPDGTIKRLIY |

FIG. 6A

| CDR2 | FR3 | CDR3 | FR4 |
|---|---|---|---|
| EI[W/C]PRSGNTYYNEKFKG | KATLTADKSSSTAYLDLRSLTSEDSAVYFCAR | HDGYPFAY | WGQGTLVTVSA |
| EIWPRSGNTYYNEKFKG | KATLTADKSSSTAYMEVRSLTSDDSAVYFCAR | HDGYPFAY | WGQGTLVTVSA |
| EIWPRSGNTYYNEKFKV | KATLSADKSSSTASMELRSLTSEDSAVYFCAR | HDGYPFAY | WGQGTLVTVSA |

| CDR2 | FR3 | CDR3 | FR4 |
|---|---|---|---|
| ATSRLHS | GVPKRFSGSRSGSDYSLTISSLEAEDFGDYYC | LQYAASPFT | FGSGTKLEIKRA |
| ATSKLHS | GVPKRFSGSRSGSDHSLTISSLEPEDLGNYYC | LQYAASPFT | FGSGTKLEIKRA |
| ATSSLDS | GVPKRFSGSRSGSDYSLTISSLESEDLVDYYC | LQYASSPWT | FGGGTKLEIKRA |

FROM FIG. 6A

FIG. 6B

| | FR1 | CDR1 | FR2 |
|---|---|---|---|
| PrP 28 | LEQSGVELARPGASVMLSCKASGYTFT (SEQ. ID NOS. 68 and 69) | TYGIS | WVKQRTGQGLEWIG |
| PrP 31 | XLGRQVMLSSKASXYTFT (SEQ. ID NOS. 75) | TYGIS | WVKQRTGQGLEWIG |
| PrP 11 | LEQSGVELARPGXSVKLSCKASGYTFT (SEQ. ID NOS. 76) | TYGIT | WVKQRTGQGLEWIG |
| PrP 20 | LEQSGVELAGPGASVKLSCKASGYTFT (SEQ. ID NOS. 77) | TYGIS | WVKQRTGQGLEWIG |
| PrP 24 | XTFT (SEQ. ID NOS. 78) | TYGIT | WVKQRTGQGLEWIG |
| PrP 26 | XYTFT (SEQ. ID NOS. 79) | TYGIT | WVKQRTGQDLEWIG |
| PrP 30 | XLSCKASGYTFT (SEQ. ID NOS. 80) | VYGIS | WVKQRTGQGLEWIG |
| PrP 32 | XTFT (SEQ. ID NOS. 81) | VYGIS | WVKQRTGQGLEWIG |
| PrP 34 | SVKLSCKASGYTFT (SEQ. ID NOS. 82) | TYGIS | WVKQRTGQGLEWIG |
| PrP 35 | ELXXPGASVKLSCKASGXTFT (SEQ. ID NOS. 83) | TYGIT | WVKQRTGQGLEWIG |
| PrP 37 | XTFT (SEQ. ID NOS. 71) | VYGIS | WVKQRTGQGLEWIG |
| PrP 38 | PGPSVKLSCKASGYTFT (SEQ. ID NOS. 84) | TYGIS | WVKQRTGQGLEWIG |
| PrP 39 | XNTFT (SEQ. ID NOS. 85) | TYGIS | WVKQRTGQGLEWIG |
| PrP 40 | XASGYTFT (SEQ. ID NOS. 86) | TYGIS | WVKQRTGQGLEWIG |

| CDR2 | FR3 | CDR3 | FR4 |
|---|---|---|---|
| EI[W/C]PRSGNTYYNEKFKG | KATLTADKSSSTAYLDLRSLTSEDSAVYFCAR | HDGYPFAY | WGQGTLVTVSA |
| EICPRSGNTYYNEKFKG | KATLTADKSSSTAYLDLRSLTSEDSAVYFCAR | HDGYPFAY | WGQGTLVTVSA |
| EIWPRSGNTYYNEKFKG | KATLTADKSSSTAYMEVRSLTSDDSAVYFCAR | HDGYPFAY | WGQGTLVTVSA |
| EIWPRSGNTYYNEKFKG | KATLTADKSSSTAYLDLRSLTSEDSAVYFCAR | HDGYPFAY | WGQGTLVTVSA |
| EIWPRSGNTYYNEKFKG | KATLTADKSSSTAYMEVRSLTSDDSAVYFCAR | HDGYPFAY | WGQGTLVTVSA |
| EIWPRSGNTYYNEKFKG | KATLTADKSSSTAYMELRSLTSDDSAVYFCAR | HDGYPFAY | WDQGTLVTVSA |
| EIWPRSGNTYYNEKFKG | KATLAADKSSSTAYMELRSLTSDDSAVYFCAR | HDGYPFAY | WGQGTLVTVST |
| EIWPRSGNTYYNEKFKV | KATLTADKSSSTAYLDLRSLTSEDSAVYFCAR | HDGYPFAY | WGQGTLVTVSA |
| EIWPRSGNTYYNEKFKV | KATLTXDKSSSTAYLDLRSLTSEDSAVYFCAR | HDGYPFAY | WGQGTLVTVST |
| EIWPRSGNTYYNEKFKG | KATLSADKSSSTAYLDLRSLTSEDSAVYFCAR | HDGYPFAY | WGQGTLVTVSA |
| EIWPRSGNTYYNEKFKG | KATLTADKSSSTAYMEVRSLTSDDSAVYFCAR | HDGYPFAY | WGQGTLVTVSA |
| EIWPRSGNTYYNEKFKV | KATLSADKSSSTASMELRSLTSEDSAVYFCAR | HDGYPFAY | WGQGTLVTVSA |
| EIWPRSGNTYYNEKFKG | KATLTADKSSSTAYLDLRSLTSEDSAVYFCAR | HDGYPFAY | WGQGTLVTVS |
| EIWPRSGNTYYNEKFKG | KATLTADKSSSTAYLDLRSLTSEDSAVYFCAR | HDGYPFAY | WGQGTLVTVSA |
| EIWPRSGNTYYNEKFKG | KATLTADKSSSTAYLDLRSLTSEDSAVYFCAR | HDGYPFAY | WGQGTLVTVSA |

FROM FIG. 7A

ANTIBODIES SPECIFIC FOR NATIVE PrP$^{Sc}$

CROSS-REFERENCE

This application is a continuation application of Ser. No. 09/036,579, filed Mar. 6, 1998, which is a divisional application of Ser. No. 08/713,939, filed Sep. 13, 1996 now issued U.S. Pat. No. 5,846,533, issued Dec. 8, 1998, which is a continuation-in-part application of Ser. No. 08/528,104, filed Sep. 14, 1995, all of which are incorporated herein by reference in their entirety and to which applications we claim priority under 35 USC §120.

GOVERNMENT RIGHTS

The United States Government may have certain rights in this application pursuant to Grant No. AGO 2132 awarded by the National Institutes of Health.

FIELD OF THE INVENTION

This invention relates to methods for obtaining antibodies and assays for using such antibodies. More specifically, the invention relates to methods of obtaining antibodies which specifically bind to naturally occurring forms of PrP$^{Sc}$.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., *Science* 218:1309–11 (1982); Prusiner, et al., *Biochemistry* 21:6942–50 (1982); McKinley, et al., *Cell* 35:57–62 (1983)]. Complete prion protein-encoding genes have since been cloned, sequenced and expressed in transgenic animals. PrP$^c$ is encoded by a single-copy host gene [Basler, et al., *Cell* 46:417–28 (1986)] and is normally found at the outer surface of neurons. Prion diseases are accompanied by the conversion of PrP$^c$ into a modified form called PrP$^{Sc}$. However, the actual biological or physiological function of PrP$^c$ is not known.

The scrapie isoform of the prion protein (PrP$^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D.C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond. (In press) (1994)*]. Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System,* Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity [Gibbs, Jr. et al., *Slow Transmissible Diseases of the Nervous System,* Vol. 2, S. B. Prusiner and W. J. Hadlow, eds. (New York: Academic Press), pp. 87–110 (1979); Tateishi, et al., *Prion Diseases of Humans and Animals,* Prusiner, et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott, et al., *Cell* 59:847–857 (1989)]. SHaPrP differs from MoPrP at 16 positions out of 254 amino acid residues [Basler, et al., *Cell* 46:417–428 (1986); Locht, et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch, et al., *N. Engl. J. Med.* 313:731–733 (1985); Brown, et al., *Lancet* 340:24–27 (1992); Fradkin, et al., *JAMA* 265:880–884 (1991); Buchanan, et al., *Br. Med. J.* 302:824–828 (1991)]. Fortunately, recombinant HGH is now used, although the seemingly remote possibility has been raised that increased expression of wtPrP$^c$ stimulated by high HGH might induce prion disease [Lasmezas, et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr., et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy, et al., *Br. J. Med.* 307:517–518 (1993); Cochius, et al., *Aust. N.Z. J. Med.* 20:592–93 (1990); Cochius, et al., *J. Neurol. Neurosurg. Psychiatry* 55:1094–1095 (1992)] as well as at least 11 patients receiving dura mater grafts [Nisbet, et al., *J. Am. Med. Assoc.* 261:1118 (1989); Thadani, et al., *J. Neurosurg.* 69:766–769 (1988); Willison, et al., *J. Neurosurg. Psychiatric* 54:940 (1991); Brown, et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist, Jul.* 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist,* Nov. 20, 1993, page 10.) Prior attempts to create PrP monoclonal antibodies have been unsuccessful (see Barry and Prusiner, J. of Infectious Diseases Vol. 154, No. 3, Pages 518–521 (1986). Thus there is a need for an assay to detect compounds which result in disease. Specifically, there is a need for a convenient, cost-effective assay for testing sample materials for the presence of prions which cause CJD. The present invention offers such an assay.

SUMMARY OF THE INVENTION

Antibodies of the invention will specifically bind to a native prion protein (i.e., native PrP$^{Sc}$) in situ with a high degree of binding affinity. The antibodies can be placed on a substrate and used for assaying a sample to determine if the sample contains a pathogenic form of a prion protein. The antibodies are characterized by one or more of the following features (1) an ability to neutralize infectious prions, (2) will bind to prion proteins (PrP$^{Sc}$) in situ i.e., will bind to naturally occurring forms of a prion protein in a cell culture or in vivo and without the need to treat (e.g., denature) the prion protein, and (3) will bind to a high percentage of the PrP$^{Sc}$ form (i.e. disease form) of prion protein in a composition e.g., will bind to 50% or more of the PrP$^{Sc}$ form of the prion proteins. Preferred antibodies are further characterized by an ability to (4) bind to a prion protein of only a specific species of mammals e.g., bind to human prion protein and not prion protein of other mammals.

An important object is to provide antibodies which bind to native prion protein (PrP$^{Sc}$).

Another object is to provide antibodies which specifically bind to epitopes of prion proteins (PrP$^{Sc}$) of a specific species of animal and not to the prion protein (PrP$^{Sc}$) of other species of animals.

Another object is to provide monoclonal antibodies which specifically bind to prion proteins (PrPSc) associated with disease, (e.g., human PrP$^{Sc}$) which antibodies do not bind to denatured PrP proteins not associated with disease (e.g., human PrP$^c$).

Still another object is to provide specific methodology to allow others to generate a wide range of specific antibodies characterized by their ability to bind one or more types of prion proteins from one or more species of animals.

Another object of the invention is to provide an assay for the detection of PrP$^{Sc}$ forms of PrP proteins.

Another object of the invention is to provide an assay which can specifically differentiate prion protein (PrP$^{Sc}$) associated with disease from PrP$^{Sc}$ not associated with disease.

Another object is to detect prions which specifically bind to native PrP$^{Sc}$ of a specific species such as a human, cow, sheep, pig, dog, cat or chicken.

An advantage of the invention is that it provides a fast, efficient cost effective assay for detecting the presence of native PrP$^{Sc}$ in a sample.

A specific advantage is that the assay can be used as a screen for the presence of prions (i.e., PrP$^{Sc}$) in products such as pharmaceuticals (derived from natural sources) food, cosmetics or any material which might contain such prions and thereby provide further assurances as to the safety of such products.

Another advantage is that the antibodies which can be used with a protease which denatures PrP$^c$ thereby providing for a means of differentiating between infectious (PrP$^{Sc}$) and non-infectious forms (PrP$^{Sc}$) of prions.

Yet another advantage of the invention is that antibodies of the invention are characterized by their ability to neutralize the infectivity of naturally occurring prions e.g., neutralize PrP$^{Sc}$.

Another advantage is that antibodies of the invention will bind to (PrP$^{Sc}$) prion proteins in situ, i.e., will bind to naturally occurring (PrP$^{Sc}$) prions in their natural state in a cell culture or in vivo without requiring that the prion proteins be particularly treated, isolated or denatured.

Another advantage is that the prion proteins of the invention will bind to a relatively high percentage of the infectious form of the prion protein (e.g., PrP$^{Sc}$)—for example bind to 50% or more of the PrP$^{Sc}$ form of prion proteins in a composition.

An important feature of the invention is that the methodology makes it possible to create a wide variety of different prion protein antibodies with the same or individually engineered features which features may make the antibody particularly suitable for uses such as (1) prion neutralization to purify a product, (2) the extraction of prion proteins and (3) therapies.

A feature of the invention is that it uses phage display libraries in the creation of the antibodies.

Another feature of the invention is that the phage are genetically engineered to express a specific binding protein of an antibody on their surface.

These and other objects, advantages, and features of the invention will become apparent to those persons skilled in the art upon reading the details of the chimeric gene, assay method, and transgenic mouse as more fully described below.

BRIEF DESCRIPTION OF THE DRAWINGS

FIG. 2 shows the amino acid sequence of mouse PrP (SEQ ID NO:1) along with specific differences between mouse PrP (SEQ ID NO:1) and human PrP (SEQ ID NO:2)

FIG. 3 shows the amino acid sequence of mouse PrP (SEQ ID NO:1) and specifically shows differences between mouse PrP (SEQ ID NO:1) and bovine PrP (SEQ ID NO:3);

FIG. 4 shows the amino acid sequence of mouse PrP and specifically shows differences between mouse PrP and bovine PrP ovine PrP (SEQ ID NO:4);

FIG. 6 shows the amino acid sequences of selected (A) heavy chain and (B) light chain variable regions generated by panning an IgG1 library from mouse D7282 against denatured MoPrP 27-30 rods;

FIG. 7 shows the deduced amino acid sequences for some of the phage clones obtained in one panning against PrP;

DETAILED DESCRIPTION OF PREFERRED EMBODIMENTS

Figure 1:
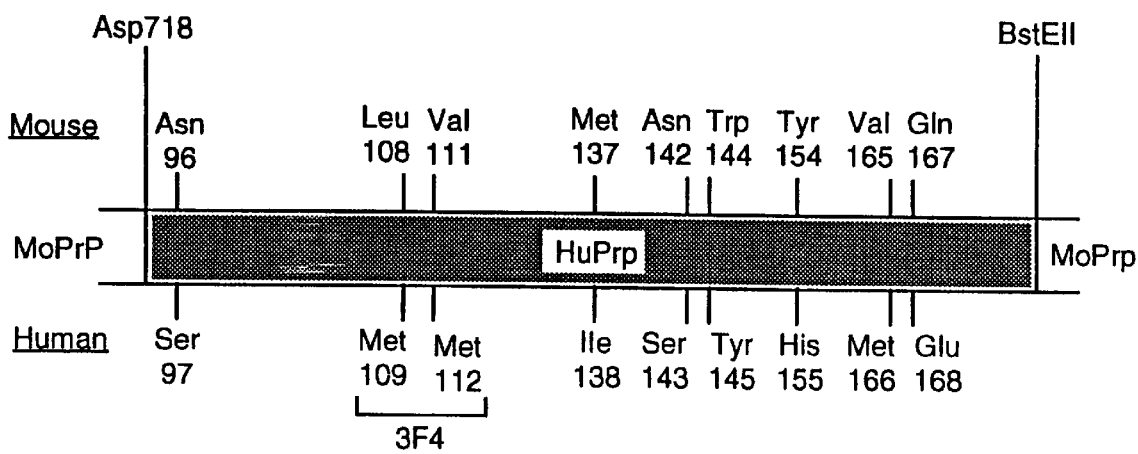
FIG. 1 is a schematic view of a portion of PrP proteins showing the differences between a normal, wild-type human PrP protein and a normal, wild-type mouse PrP protein.

Before the present antibodies, assays and methods for producing an using such are disclosed and described, it is to be understood that this invention is not limited to particular antibodies, assays or method as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the is publications are cited.

The terms "PrP protein", "PrP" and the like are used interchangeably herein and shall mean both the infectious particle form $PrP^{Sc}$ known to cause diseases (spongiform encephalopathies) in humans and animals and the non-infectious form $PrP^c$ which, under appropriate conditions is converted to the infectious $PrP^{Sc}$ form.

The terms "prion", "prion protein" and "$PrP^{Sc}$ protein" and the like used interchangeably herein to refer to the infectious $PrP^{Sc}$ form of a PrP protein and is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The term "PrP gene" is used herein to describe genetic material which expresses proteins as shown in FIGS. 2–4 and polymorphisms and mutations such as those listed herein under the subheading "Pathogenic Mutations and Polymorphisms." The term "PrP gene" refers generally to any gene of any species which encodes any form of a prion protein. Some commonly known PrP sequences are described in Gabriel et al., *Proc. Natl. Acad. Sci. USA* 89:9097–9101 (1992) which is incorporated herein by reference to disclose and describe such sequences. The PrP gene can be from any animal including the "host" and "test" animals described herein and any and all polymorphisms and mutations thereof, it being recognized that the terms include other such PrP genes that are yet to be discovered. The protein expressed by such a gene can assume either a $PrP^c$ (non-disease) of $PrP^{Sc}$ (disease) form.

The terms "standardized prion preparation", "prion preparation", "preparation" and the like are used interchangeably herein to describe a composition containing prions ($PrP^{Sc}$) which composition is obtained from brain tissue of mammals which contain substantially the same genetic material as relates to prions, e.g., brain tissue from a set of mammals which exhibit signs of prion disease which mammals (1) include a transgene as described herein; (2) have an ablated endogenous prion protein gene; (3) have a high copy number of prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease due to their genetically modified make up, e.g., high copy number of prion protein genes.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 2, 3 and 4 with one or more different replacement codons selected from the codons shown in these Figures for humans, cows and sheep replacing mouse codons at the same relative position, with the proviso that not all the mouse codons are replaced with differing human, cow or sheep codons. Artificial PrP genes can include not only codons of genetically diverse animals but may include codons and codon sequences not associated with any native PrP gene but which, when inserted into an animal render the animal susceptible to infection with prions which would normally only infect a genetically diverse animal.

The terms "chimeric gene," "chimeric PrP gene", "chimeric prion protein gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The term "genetic material related to prions" is intended to cover any genetic material which effects the ability of an animal to become infected with prions. Thus, the term encompasses any "PrP gene", "artificial PrP gene", "chimeric PrP gene" or "ablated PrP gene" which terms are defined herein as well as modification of such which effect the ability of an animal to become infected with prions. Standardized prion preparations are produced using animals which all have substantially the same genetic material related to prions so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their PrP gene ablated i.e., rendered inoperative. The host is inoculated with prion proteins to generate antibodies. The cells producing the antibodies are a source of genetic material for making a phage library. Other host animals may have a natural (PrP) gene or one which is altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP protein gene", "disrupted PrP gene", and the like are used interchangeably herein to mean an endogenous PrP gene which has been altered (e.g., add and/or remove nucleotides) in a manner so as to render the gene inoperative. Examples of non-functional PrP genes and methods of making such are disclosed in Bueler, H., et al "Normal development of mice lacking the neuronal cell-surface PrP protein" *Nature* 356, 577–582 (1992) and Weisman (WO 93/10227). The methodology for ablating a gene is taught in Capecchi, *Cell* 51:503–512 (1987) all of which are incorporated herein by reference. Preferably both alleles of the genes are disrupted.

The terms "hybrid animal", "transgenic hybrid animal" and the like are used interchangeably herein to mean an animal obtained from the cross-breeding of a first animal having an ablated endogenous prion protein gene with a second animal which includes either (1) a chimeric gene or artificial PrP gene or (2) a PrP gene from a genetically diverse animal. For example a hybrid mouse is obtained by cross-breeding a mouse with an ablated mouse gene with a mouse containing (1) human PrP genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species. A hybrid animal can be inoculated with prions and serve as a source of cells for the creation of hybridomas to make monoclonal antibodies of the invention.

The terms "susceptible to infection" and "susceptible to infection by prions" and the like are used interchangeably herein to describe a transgenic or hybrid test animal which develops a disease if inoculated with prions which would normally only infect a genetically diverse test animal. The terms are used to describe a transgenic or hybrid animal such as a transgenic mouse Tg(MHu2M) which, without the chimeric PrP gene, would not become infected with a human prion but with the chimeric gene is susceptible to infection with human prions.

By "antibody" is meant an immunoglobulin protein which is capable of binding an antigen. Antibody as used herein is meant to include the entire antibody as well as is any antibody fragments (e.g. F(ab')$_2$, Fab', Fab, Fv) capable of binding the epitope, antigen or antigenic fragment of interest.

Antibodies of the invention are immunoreactive or immunospecific for and therefore specifically and selectively bind to a PrP$^{Sc}$ protein. Antibodies which are immunoreactive and immunospecific for natural or native PrP$^{Sc}$ are preferred. Antibodies for PrP$^{Sc}$ are preferably immunospecific—i.e., not substantially cross-reactive with related materials. Although the term "antibody" encompasses all types of antibodies (e.g., monoclonal) the antibodies of the invention are preferably produced using the phage display methodology described herein.

By "purified antibody" is meant one which is sufficiently free of other proteins, carbohydrates, and lipids with which it is naturally associated. Such an antibody "preferentially binds" to a native PrP$^{Sc}$ protein (or an antigenic fragment thereof), i.e., does not substantially recognize and bind to other antigenically-unrelated molecules. A purified antibody of the invention is preferably immunoreactive with and immunospecific for a PrP$^{Sc}$ protein of specific species and more preferably immunospecific for native human PrP$^{Sc}$.

By "antigenic fragment" of a PrP protein is meant a portion of such a protein which is capable of binding an antibody of the invention.

By "binds specifically" is meant high avidity and/or high affinity binding of an antibody to a specific polypeptide i.e., epitope of a PrP$^{Sc}$ protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to PrP$^{Sc}$ than denatured fragments of PrP$^c$ so that by adjusting binding conditions the antibody binds almost exclusively to PrP$^{Sc}$ and not denatured fragments of PrP$^C$. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to native PrPs$^{Sc}$ in situ with a binding affinity of $10^7$ mole/1 or more, preferably $10^8$ mole/liters or more are said to bind specifically to PrP$^{Sc}$. In general, an antibody with a binding affinity of $10^6$ mole/liters or less is not useful in that it will not bind an antigen at a detectable level using conventional methodology currently used.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labelling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The invention is directed toward treating patients with infectious prions and is particularly directed toward treating humans infected with $PrP^{Sc}$, resulting in a disease of the central nervous system such as bovine spongiform encephalopathy; Creutzfeldt-Jakob Disease; fatal familial insomnia or Gerstmann-Strassler-Scheinker Disease.

Abbreviations used herein include:

CNS for central nervous system;
BSE for bovine spongiform encephalopathy;
CJD for Creutzfeldt-Jakob Disease;
FFI for fatal familial insomnia;
GSS for Gerstmann-Strassler-Scheinker Disease;
Hu for human;
HuPrP for a human prion protein;
Mo for mouse;
MoPrP for a mouse prion protein;
SHa for a Syrian hamster;
SHaPrP for a Syrian hamster prion protein;
Tg for transgenic;
Tg(SHaPrP) for a transgenic mouse containing the PrP gene of a Syrian hamster;
Tg(HuPrP) for transgenic mice containing the complete human PrP gene;
Tg(ShePrP) for transgenic mice containing the complete sheep PrP gene;
Tg(BovPrP) for transgenic mice containing the complete cow PrP gene;
$PrP^{Sc}$ for the scrapie isoform of the prion protein;
$PrP^C$ for the cellular contained comon, normal isoform of the prion protein;
$MoPrP^{Sc}$ for the scrapie isoform of the mouse prion protein;
MHu2M for a chimeric mouse/human PrP gene wherein a region of the mouse PrP gene is replaced by a corresponding human sequence which differs from mouse PrP at 9 codons;
Tg(MHu2M) mice are transgenic mice of the invention which include the chimeric MHu2M gene;
$MHu2MPrP^{Sc}$ for the scrapie isoform of the chimeric human/mouse PrP gene;
$PrP^{CJD}$ for the CJD isoform of a PrP gene;
$Prnp^{0/0}$ for ablation of both alleles of an endogenous prion protein gene, e.g., the MoPrP gene;
$Tg(SHaPrP^{+/0})$ for a particular line (81) of transgenic mice expressing SHaPrP, +/0 indicates heterozygous;
$Tg(HuPrP)/Prnp^{0/0}$ for a hybrid mouse obtained by crossing a mouse with a human prion protein gene (HuPrP) with a mouse with both alleles of the endogenous prion protein gene disrupted;

Tg(MHu2M) Prnp$^{0/0}$ for a hybrid mouse obtained by crossing a mouse with a chimeric prion protein gene (MHu2M) with a mouse with both alleles of the endogenous prion protein gene disrupted.

FVB for a standard inbred strain of mice often used in the production of transgenic mice since eggs of FVB mice are relatively large and tolerate microinjection of exogenous DNA relatively well.

GENERAL ASPECT OF THE INVENTION

The core of the invention is an antibody which specifically binds to a PrP$^{Sc}$ protein and preferably binds to a native non-denatured PrP$^{Sc}$ protein in situ with an affinity of $10^7$ moles/liter or more, preferable $10^8$ a moles/liter or more of a single species (e.g., human) and more preferably binds only to human PrP$^{Sc}$ and not denatured fragments of human PrP$^{C}$). The antibody may bind to all proteins coded by the different mutations and/or polymorphisms of the PrP protein gene. Alternatively, a battery of antibodies (2 or more different antibodies) are provided wherein each antibody of the battery specifically binds to protein coded by a different mutation or polymorphism of the PrP gene. The antibody can be bound to support surface and used to assay a sample in vitro for the presence of a particular type of human $PrP^{Sc}$. The antibody can also be bound to a detectable label and injected into an animal to assay in vivo for the presence of a particular type of native $PrP^{Sc}$.

Although there are known procedures for producing antibodies from any given antigen practice has shown that it is particularly difficult to produce antibodies which bind to certain proteins e.g., $PrP^{Sc}$. The difficulty with obtaining antibodies to $PrP^{Sc}$ relates, in part, to its special and unknown qualities. By following procedures described herein antibodies which bind native $PrP^{Sc}$ in situ have been obtained and others may follow the procedures described here to obtain other antibodies to $PrP^{Sc}$ and to other proteins for which it is difficult to generate antibodies.

To produce antibodies of the invention it is preferable to begin with inoculating a host mammal with prion proteins i.e., infectious $PrP^{Sc}$. The host mammal may be any mammal and is preferably a host mammal of the type defined herein such as a mouse, rat, guinea pig or hamster and is most preferably a mouse. The host animal is inoculated with prion proteins which are endogenous to a different species which is preferably a genetically diverse species. For example a mouse is inoculated with human prion proteins. Preferably, the host mammal is inoculated with infectious prion proteins of a genetically diverse mammal. For example, a mouse is inoculated with human $PrP^{Sc}$. Using a normal host mammal in this manner it is possible to elicit the generation of some antibodies. However, when a hosts animal includes a prion protein gene and is inoculated with prions from a genetically diverse species antibodies will, if at all, only be generated for epitopes which differ between epitopes of the prion protein of the host animal and epitopes of the genetically diverse species. This substantially limits the amount of antibodies which might be generated and decreases the ability to find an antibody which selectively binds to an infectious form of a prion protein and does not bind to denatured fragments of a non-infectious form. Thus, unless one is attempting to generate antibodies which differentiate between prion proteins of different species it is preferable to begin the antibody production process using a mammal which has an ablated prion protein gene i.e., a null PrP gene abbreviated as $Prnp^{0/0}$. Accordingly, the invention is generally described in connection with the use of such "null" mammals and specifically described in connection with "null mice."

Antibodies are produced by first producing a host animal (e.g., a mouse) which has its endogenous PrP gene ablated, i.e., the PrP gene rendered inoperative. A mouse with an ablated PrP gene is referred to as a "null mouse". A null mouse can be created by inserting a segment of DNA into a normal mouse PrP gene and/or removing a portion of the gene to provide a disrupted PrP gene. The disrupted gene is injected into a mouse embryo and via homologous recombination replaces the endogenous PrP gene.

The null mouse is injected with prions in order to stimulate the formation of antibodies. Further, injections of adjuvants and prions are generally used to maximize the generation of antibodies.

The mouse is then sacrificed and bone marrow and spleen cells are removed. The cells are lysed, RNA is extracted and reversed transcribed to cDNA. Antibody heavy and light chains (or parts thereof) and then amplified by PCR. The amplified cDNA library may be used as is or after manipulation to create a range of variants and thereby increase the size of the library.

An IgG phage display library is then constructed by inserting the amplified cDNA encoding IgG heavy chain and the amplified cDNA encoding a light chain into a phage display vector (e.g., a pComb3 vector) such that one vector contains a cDNA insert encoding a heavy chain fragment in a first expression cassette of the vector, and a cDNA insert encoding a light chain fragment in a second expression cassette of the vector.

Ligated vectors are then packaged by filamentous phage M13 using methods well known in the art. The packaged library is then used to infect a culture of *E. coli,* so as to amplify the number of phage particles. After bacterial cell lysis, the phage particles are isolated and used in a panning procedure.

The library created is panned against a composition containing prions. Antibody fragments which selectively bind to $PrP^{Sc}$ e.g., human $PrP^{Sc}$ are then isolated.

Specifics of a PrP Protein

The major component of purified infectious prions, designated PrP 27-30, is the proteinase K resistant core of a larger native protein $PrP^{Sc}$ which is the disease causing form of the ubiquitous cellular protein $PrP^C$. $PrP^{Sc}$ is found only in scrapie infected cells whereas $PrP^C$ is present in both infected and uninfected cells implicating $PrP^{Sc}$ as the major, if not the sole, component of infectious prion particles. Since both $PrP^C$ and $PrP^{Sc}$ are encoded by the same single copy gene, great effort has been directed toward unraveling the mechanism by which $PrP^{Sc}$ is derived from $PrP^C$. Central to this goal has been the characterization of physical and chemical differences between these two molecules. Properties distinguishing $PrP^{Sc}$ from $PrP^C$ include low solubility (*Meyer, et al* 1986 *PNAS*), poor antigenicity (Kascack, *J. Virol* 1987; Serban D. 1990) protease resistance (Oesch. et al 1985 *Cell*) and polymerization of PrP 27-30 into rod-shaped aggregates which are very similar, on the ultrastructural and histochemical levels, to the PrP amyloid plaques seen in scrapie diseased brains (Prusiner, et al *Cell* 1983). By using proteinase K it is possible to denature $PrP^C$ but not $PrP^{Sc}$.To date, attempts to identify any post-transitional chemical modifications in $PrP^C$ that lead to its conversion to $PrP^{Sc}$ have proven fruitless (Stahl, et al 1993 *Biochemistry*). Consequently, it has been proposed that $PrP^C$ and $PrP^{Sc}$ are in fact conformational isomers of the same molecule.

Conformational description of PrP using conventional techniques has been hindered by problems of solubility and the difficulty in producing sufficient quantities of pure protein. However, PrP$^C$ and PrP$^{Sc}$ are conformationally distinct. Theoretical calculations based upon the amino acid sequences of PrPs from several species have predicted four putative helical motifs in the molecule. Experimental spectroscopic data would indicate that in PrP$^C$ these regions adopt α-helical arrangements, with virtually no β-sheet (Pan, et al PNAS 1993). In dramatic contrast, in the same study it was found that PrP$^{Sc}$ and PrP 27-30 possess significant β-sheet content, which is typical of amyloid proteins. Moreover, studies with extended synthetic peptides, corresponding to PrP amino acid residues 90–145, have demonstrated that these truncated molecules may be converted to either α-helical or β-sheet structures by altering their solution conditions. The transition of PrP$^C$ to PrP$^{Sc}$ requires the adoption of β-sheet structure by regions that were previously α-helical.

In general, scrapie infection fails to produce an immune response, with host organisms being tolerant to PrP$^{Sc}$ from the same species. Polyclonal anti-PrP antibodies have though been raised in rabbits following immunization with large amounts of SHaPrP 27-30 (Bendheim, et al PNAS 1985, Bode, et al J. Gen. Virol. 1985). Similarly, a handful of anti-PrP monoclonal antibodies have been produced in mice (Kascack, et al, J. Virol. 1987, Barry, et al, J. Infect. Dis. 1986). These antibodies are able to recognize native PrP$^C$ and denatured PrP$^{Sc}$ from both SHa and humans equally well, but do not bind to MoPrP. Unsurprisingly, the epitopes of these antibodies were mapped to regions of sequence containing amino acid differences between SHa- and MoPrP (Rogers, et al, J. Immunol. 1993).

It is not entirely clear as to why antibodies of the type described in the above cited publications will bind to PrP$^C$ but not to PrP$^{Sc}$. Without being bound to any particular theory it is suggested that such may take place because epitopes which are exposed when the protein is in the PrP$^C$ conformation are unexposed or partially hidden in the PrP$^{Sc}$ configuration—where the protein is relatively insoluble and more compactly folded together. It is pointed out that stating that an antibody binds to PrP$^C$ but not to PrP$^{Sc}$ is not correct in absolute terms (but correct in commonly accepted terms) because some minimal binding to PrP$^{Sc}$ may occur. For purposes of the invention an indication that no binding occurs means that the equilibrium or affinity constant $K_a$ is $10^6$ l/mole or less. Further, binding will be recognized as existing when the $K_a$ is at $10^7$ l/mole or greater preferably $10^8$ l/mole or greater. The binding affinity of $10^7$ l/mole or more may be due to (1) a single monoclonal antibody (i.e., large numbers of one kind of antibodies) (2) a plurality of different monoclonal antibodies (e.g., large numbers of each of five different monoclonal antibodies) or (3) large numbers of polyclonal antibodies. It is also possible to use combinations or (1)–(3).

Preferred antibodies will bind 50% or more of the PrP$^{Sc}$ in a sample. However, this may be accomplished by using several different antibodies as per (1)–(3) above. It has been found that an increased number of different antibodies is more effective in binding a larger percentage of the PrP$^{Sc}$ in a sample as compared to the use of a single antibody. For example, the use of six copies of a single antibody "Q" might bind 40% of the PrP$^{Sc}$ in a sample. Similar results might be obtained with six copies of antibody "R" and "S". However, by using two copies each of "Q", "R" and "S" the six antibodies will bind over 50% of the $PrP^{Sc}$ in a sample. Thus, a synergistic effect can be obtained by combining combinations of two or more antibodies which bind $PrP^{Sc}$ i.e., by combining two or more antibodies which have a binding affinity $K_a$ for $PrP^{Sc}$ of $10^7$ l/mole or more. Thus combination of D4, R2, 6D2, D14, R1 and R10 and/or related antibodies can provide synergistic results.

Antibody/Antigen Binding Forces

The forces which hold an antigen and antibody together are in essence no different from non-specific interactions which occur between any two unrelated proteins i.e., other macromolecules such as human serum albumin and human transferrin. These intermolecular forces may be classified into four general areas which are (1) electrostatic; (2) hydrogen bonding; (3) hydrophobic; and (4) Van der Waals. Electrostatic forces are due to the attraction between oppositely charged ionic groups on two protein side-chains. The force of attraction (F) is inversely proportional to the square of the distance (d) between the charges. Hydrogen bonding forces are provided by the formation of reversible hydrogen bridges between hydrophilic groups such as —OH, $—NH_2$ and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalatnine tend to associate in an aqueous environment. Lastly, Van der Waals are forces created between molecules which depend on interaction between the external electron clouds.

Further information regarding each of the different types of forces can be obtained from "Essential Immunology" edited by I. M. Roitti (6th Edition) Blackwell Scientific Publications, 1988. With respect to the present invention useful antibodies exhibit all of these forces. It is by obtaining an accumulation of these forces in larger amounts that it is possible to obtain an antibody which has a high degree of affinity or binding strength to the PrP protein and in particular an antibody which has a high degree of binding strength to $PrP^{Sc}$ in situ.

Measuring Antibody/Antigen Binding Strength

The binding affinity between an antibody and an antigen can be measured which measurement is an accumulation of a measurement of all of the forces described above. Standard procedures for carrying out such measurements exist and can be directly applied to measure the affinity of antibodies of the invention for PrP proteins including native $PrP^{Sc}$ in situ.

One standard method for measuring antibody/antigen binding affinity is through the use of a dialysis sac which is a container comprised of a material which is permeable to the antigen but impermeable to the antibody. Antigens which are bound completely or partially to antibodies are placed within the dialysis sac in a solvent such as in water. The sac is then placed within a larger container which does not contain antibodies or antigen but contains only the solvent e.g., the water. Since only the antigen can diffuse through the dialysis membrane the concentration of the antigen within the dialysis sac and the concentration of the antigen within the outer larger container will attempt to reach an equilibrium. After placing the dialysis sac into the larger container and allowing for time to pass towards reaching an equilibrium it is possible to measure the concentration of the antigen within the dialysis sac and within the surrounding container and then determine the differences in concentration. This makes it possible to calculate the amount of antigen which remains bound to antibody in the dialysis sac and the amount: which disassociates from the antibody and diffuses into the surrounding container. By constantly renewing the solvent (e.g., the water) within the surrounding container so as to remove any antigen which is diffused thereinto it is possible to totally disassociate the antibody from antigen within the dialysis sac. If the surrounding solvent is not renewed the system will reach an equilibrium and it is possible to calculate the equilibrium constant (K) of the reaction i.e., the association and disassociation between the antibody and antigen. The equilibrium constant (K) is calculated as an amount equal to the concentration of antibody bound to antigen within the dialysis sac divided by the concentration of free antibody combining sites times the concentration of free antigen. The equilibrium constant or "K" value is generally measured in terms of liters per mole. The K value is a measure of the difference in free energy (deta g) between the antigen and antibody in the free state as compared with the complexed form of the antigen and antibody. When using the phage display methodology described below the antibodies obtained have an affinity or K value of $10^7$ mole/liter or more.

Antibody Avidity

As indicated above the term "affinity" describes the binding of an antibody to a single antigen determinate. However, in most practical circumstances one is concerned with the interaction of an antibody with a multivalent antigen. The term "avidity" is used to express this binding. Factors which contribute to avidity are complex and include the heterogeneity of the antibodies in a given serum which are directed against each determinate on the antigen and the heterogeneity of the determinants themselves. The multivalence of most antigens leads to an interesting "bonus" effect in which the binding of two antigen molecules by an antibody is always greater, usually many fold greater, than the arithmetic sum of the individual antibody links. Thus, it can be understood that the measured avidity between an antiserum and a multivalent antigen will be somewhat greater than the affinity between an antibody and a single antigen determinate.

Null PrP Mice to Make Antibodies

The present invention circumvents problems of tolerance and more efficiently generates panels of monoclonal antibodies capable of recognizing diverse epitopes on Mo and other PrPs in part using mice with both alleles of the PrP gene (Prnp) are ablated (Prnp$^{0/0}$) (Bueler, et al, 1992). These PrP-deficient mice (or null mice), are indistinguishable from normal mice in their development and behavior. These null mice are resistant to scrapie following intracerebral inoculation of infectious MoPrP$^{Sc}$ (Bueler, et al, 1993 *Cell;* Prusiner, et al, *PNAS* 1993). In addition Prnp$^{0/0}$ mice will develop IgG serum titers against Mo—, SHa and human PrP following immunization with relatively small quantities of purified SHaPrP 27-30 in adjuvant (Prusiner, et al, *PNAS* 1993). After allowing sufficient time to generate antibodies the immunized Prnp$^{0/0}$ mice were sacrificed for hybridoma production in the conventional manner. Fusions derived from these mice did secrete PrP specific antibody. However, these hybridomas would not secrete PrP specific antibodies for more than a few hours. In view of the somewhat limited success a different approach was taken.

Phage Display

Combinatorial antibody library technology, i.e., antigen based selection from antibody libraries expressed on the surface of M13 filamentous phage, offers a new approach to the generation of monoclonal antibodies and possesses a number of advantages relative to hybridoma methodologies which are particularly pertinent to the prion problem (Huse, et al, 1989; Barba, et al. 1991; Clackson, et al. 1991; Burton and Barbas, 1994). The present invention uses such technology to provide PrP-specific monoclonal antibodies from phage antibody libraries prepared from MoPrP-immunized Prnp$^{0/0}$ mice. The invention provides the first monoclonal antibodies recognizing MoPrP in situ and demonstrates the application of combinatorial libraries for cloning specific antibodies from null mice. The general methodologies involved in creating large combinatorial libraries using phage display technology is described and disclosed in U.S. Pat. No. 5,223,409 issued Jun. 29, 1993 which patent is incorporated herein by reference to disclose and describe phage display methodology.

Null Animals

The invention is largely described herein with respect to null mice i.e., FVB mice with both alleles of the PrP gene ablated. However, other host animals can be used and preferred host animals are mice and hamsters, with mice being most preferred in that there exists considerable knowledge on the production of transgenic animals. Possible host animals include those belonging to a genus selected from Mus (e.g. mice), Rattus (e.g. rats), Oryctolagus (e.g. rabbits), and Mesocricetus (e.g. hamsters) and Cavia (e.g., guinea pigs). In general mammals with a normal full grown adult body weight of less than 1 kg which are easy to breed and maintain can be used.

PrP Gene

The genetic material which makes up the PrP gene is known for a number of different species of animals (see Gabriel et al., *Proc. Natl. Acad. Sci. USA* 89:9097–9101 (1992)). Further, there is considerable homology between the PrP genes in different mammals. For example, see the amino acid sequence of mouse PrP compared to human, cow and sheep PrP in FIGS. 2, 3 and 4 wherein only the differences are shown. Although there is considerable genetic homology with respect to PrP genes,, the differences are significant in some instances. More is specifically, due to small differences in the protein encoded by the PrP gene of different mammals, a prion which will infect one mammal (e.g. a human) will not normally infect a different mammal (e.g. a mouse). Due to this "species barrier", it is not generally possible to use normal animals, (i.e., animal which have not had their genetic material related to PrP proteins manipulated) such as mice to determine whether a particular sample contains prions which would normally infect a different species of animal such as a human. The present invention solves this problem by providing antibodies which bind to native PrP$^{Sc}$ proteins of any species of animal for which the antibody is designed.

Pathogenic Mutations and Polymorphisms

There are a number of known pathogenic mutations in the human PrP gene. Further, there are known polymorphisms in the human, sheep and bovine PrP genes. The following is a list of such mutations and polymorphisms:

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |

-continued

| Pathogenic human mutations | Human Polymorphisms | Sheep Polymorphisms | Bovine Polymorphisms |
|---|---|---|---|
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

The DNA sequence of the human, sheep and cow PrP genes have been determined allowing, in each case, the prediction of the complete amino acid sequence of their respective PrP proteins. The normal amino acid sequence which occurs in the vast majority of individuals is referred to as the wild-type PrP sequence. This wild-type sequence is subject to certain characteristic polymorphic variations. In the case of human PrP (SEQ ID NO:2), two polymorphic amino acids occur at residues 129 (Met/Val) and 219 (Glu/Lys). Sheep PrP (SEQ ID NO:4) has two amino acid polymorphisms at residues 171 and 136, while bovine PrP (SEQ ID NO:3) has either five or six repeats of an eight amino acid motif sequence in the amino terminal region of the mature prion protein. While none of these polymorphisms are of themselves pathogenic, they appear to influence prion diseases. Distinct from these normal variations of the wild-type PrP proteins, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

"Strains" of Human Prions

Studies in rodents have shown that prion strains produce different patterns of $PrP^{Sc}$ accumulation [Hecker et al., *Genes & Development* 6:1213–1228 (1992); DeArmond et al., *Proc. Natl. Acad. Sci. USA* 90:6449–6453 (1993)]; which can be dramatically changed by the sequence of $PrP^{Sc}$ [Carlson et al., *Proc. Natl. Acad. Sci. USA* in press (1994)]. The molecular basis of prion diversity has for many years been attributed to a scrapie specific nucleic acid [Bruce et al., *J. Gen. Virol.* 68:79–89 (1987)] but none has been found [Meyer et al., *J. Gen. Virol.* 72:37–49 (1991); Kellings et al., *J. Gen. Virol.* 73:1025–1029 (1992)]. Other hypotheses to explain prion strains include variations in PrP Asn-linked sugar chains [Hecker et al., *Genes & Development* 6:1213–1228 (1992)] and multiple conformers of $PrP^{Sc}$ [Prusiner, S. B., *Science* 252:1515–1522 (1991)]. The patterns of $PrP^{Sc}$ in Tg(MHu2M) mice were remarkably similar for the three inocula from humans dying of CJD.

The patterns of $PrP^{Sc}$ accumulation in the brains of inoculated Tg(MHu2M) mice were markedly different for RML prions and Hu prions. However, RML prion inocula containing $MoPrP^{Sc}$ stimulated the formation of more $MoPrP^{Sc}$ while Hu prion inocula containing $HuPrP^{CJD}$ triggered production of $MHu2MPrP^{Sc}$. The distribution of neuropathological changes characterized by neuronal vacuolation and astrocytic gliosis is similar to the patterns of $PrP^{Sc}$ accumulation in the brains of Tg(MHu2M) mice inoculated with RML prions or Hu prions.

Standardized Prion Preparation

Standardized prion preparations may be produced in order to test assays of the invention and thereby improve the reliability of the assay. Although the preparation can be obtained from any animal it is preferably obtained from a host animal which has brain material containing prions of a test animal. For example, a transgenic mouse containing a human prion protein gene can produce human prions and the brain of such a mouse can be used to create a standardized human prion preparation. Further, in that the preparation is to be a "standard" it is preferably obtained from a battery (e.g., 100; 1,000, or more animals) of substantial identical animals. For example, 100 mice all containing a very high copy number of human PrP genes (all polymorphisms and mutations) would spontaneously develop disease and the brain tissue from each could be combined to make a useful standardized prion preparation.

Standardized prion preparations can be produced using any of modified host mammals of the type described above. For example, standardized prion preparations could be produced using mice, rats, hamsters, or guinea pigs which are genetically modified so that they are susceptible to infection with prions which prions would generally only infect genetically diverse species such as a human, cow, sheep or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals. Details regarding making standardized prion preparation are described in U.S. patent application entitled "Method of Detecting Prions in a Sample and Transgenic Animal Used For Same", filed Aug. 31, 1995, Ser. No. 08/521,992 and U.S. patent application entitled "Detecting Prions In A Sample And Prion Preparation And Transgenic Animal Used For Same", filed Jul. 30, 1996, both of which applications are incorporated herein by reference.

Once an appropriate type of host is chosen, such as a mouse, the next step is to choose the appropriate type of genetic manipulation to be utilized to produce a standardized prion formulation. For example, the mice may be mice which are genetically modified by the insertion of a chimeric gene of the invention. Within this group the mice might be modified by including high copy numbers of the chimeric gene and/or by the inclusion of multiple promoters in order to increase the level of expression of the chimeric gene. Alternatively, hybrid mice of the invention could be used wherein mice which have the endogenous PrP gene ablated are crossed with mice which have a human PrP gene inserted into their genome. There are, of course, various subcategories of such hybrid mice. For example, the human PrP gene may be inserted in a high copy number an/or used with multiple promoters to enhance expression. In yet another alternative the mice could be produced by inserting multiple different PrP genes into the genome so as to create mice which are susceptible to infection with a variety of different prions, i.e., which generally infect two or more types of test animals. For example, a mouse could be created which included a chimeric gene including part of the sequence of a human, a separate chimeric gene which included part of the sequence of a cow and still another chimeric gene which included part of the sequence of a sheep. If all three different types of chimeric genes were inserted into the genome of the mouse the mouse would be susceptible to infection with prions which generally only infect a human, cow and sheep.

After choosing the appropriate mammal (e.g., a mouse) and the appropriate mode of genetic: modification (e.g., inserting a chimeric PrP gene) the next step is to produce a large number of such mammals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g., within ±30 days of each other.

Once a large group e.g., 50 or more, more preferably 100 or more, still more preferably 500 or more of such mice are produced. The next step is to inoculate the mice with prions which generally only infect a genetically diverse mammal e.g., prions from a human, sheep, cow or horse. The amounts given to different groups of mammals could be varied. After inoculating the mammals with the prions the mammals are observed until the mammals exhibit symptoms of prion infection e.g., clinical signs of CNS dysfunction. After exhibiting the symptoms of prion infection the brain or at least a portion of the brain tissue of each of the mammals is extracted. The extracted brain tissue is homogenized which provides the standardized prion preparation.

As an alternative to inoculating the group of transgenic mice with prions from a genetically diverse animal it is possible to produce mice which spontaneously develop prion related diseases. This can be done, for example, by including extremely high copy numbers of a human PrP gene into a mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce a standardized prion preparation.

The standardized prion preparations can be used directly or can be diluted and tittered in a manner so as to provide for a variety of different positive controls. More specifically, various known amounts of such standardized preparation can be used to inoculate a first set of transgenic control mice. A second set of substantially identical mice are inoculated with a material to be tested i.e., a material which may contain prions. A third group of substantially identical mice are not injected with any material. The three groups are then observed. The third group, should, of course not become ill in that the mice are not injected with any material. If such mice do become ill the assay is not accurate probably due to the result of producing mice which spontaneously develop disease. If the first group, injected with a standardized preparation, do not become ill the assay is also inaccurate probably because the mice have not been correctly created so as to become ill when inoculated with prions which generally only infect a genetically diverse mammal. However, if the first group does become ill and the third group does not become ill the assay can be presumed to be accurate. Thus, if the second group does not become ill the test material does not contain prions and if the second group does become ill the test material does contain prions.

By using standardized prion preparations of the invention it is possible to create extremely dilute compositions containing the prions. For example, a composition containing one part per million or less or even one part per billion or less can be created. Such a composition can be used to test the sensitivity of the antibodies, assays and methods of the invention in detecting the presence of prions.

Prion preparations are desirable in that they will include a constant amount of prions and are extracted from an isogeneic background. Accordingly, contaminates in the preparations will be constant and controllable. Standardized prion preparations will be useful in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations will be valuable in validating purification protocols where preparations are spiked and reductions in teeter measured for a particular process.

Useful Applications

As indicated above and described further below in detailed examples it is possible to use the methodology of the invention to create a wide range of different antibodies. i.e., antibodies having different specific features. For example, antibodies can be created which bind only to a prion protein naturally occurring within a single species and not bind to a prion protein naturally occurring within other species. Further, the antibody can be designed so as to bind only to an infectious form of a prion protein (e.g., $PrP^{Sc}$) and not bind to a non-infectious form (e.g., $PrP^{C}$). A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a sample in vitro to determine if the sample contains one or more types of antibodies. For example, antibodies which bind only to human PrP$^{Sc}$ can be attached to the surface of a material and a sample can be denatured via proteinase K. The denatured sample is brought into contact with the antibodies bound to the surface of material. If no binding occurs it can be deduced that the sample does not contain human PrP$^{Sc}$.

Antibodies of the invention are also characterized by their ability to neutralize prions. Specifically, when antibodies of the invention are allowed to bind to prions the infectivity of the prion is eliminated. Accordingly, antibody compositions of the invention can be added to any given product in order to neutralize any infectious prion protein within the product. Thus, if a product is produced from a natural source which might contain infectious prion proteins the antibodies of the invention could be added as a precaution thereby eliminating any potential infection resulting from infectious prion proteins.

The antibodies of the invention can be used in connection with immunoaffinity chromatography technology. More specifically, the antibodies can be placed on the surface of a material within a chromatography column. Thereafter, a composition to be purified can be passed through the column. If the sample to be purified includes any prion protein which binds to the antibodies those prion proteins ($PrP^{Sc}$) will be removed from the sample and thereby purified.

Lastly, the antibodies of the invention can be used to treat a mammal. The antibodies can be given prophylactically or be administered to an individual already infected with infectious prion proteins such infection having been determined by the use of the assay described above. The exact amount of antibody to be administered will vary depending on a number of factors such as the age, sex, weight and condition of the patient. Those skilled in the art can determine the precise amount by administering antibodies in small amounts and determining the effect and thereafter adjusting the dosage. It is suggested that the dosage can vary from 0.01 mg/kg to about 300 mg/kg, preferably about 0.1 mg/kg to about 200 mg/kg, more preferably about 0.2 mg/kg to about 20 mg/kg in one or more dose administrations daily, for one or several days. Preferred is administration of the antibody for 2 to 5 or more consecutive days in order to avoid "rebound" of prion infectivity occurring.

EXAMPLES

The following examples are put forth so as to provide those of ordinary skill in the art with a complete disclosure and description of how to make and use the chimeric genes, transgenic mice and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Construction of Phage Display Antibody Libraries Expressing Antibodies (Fabs)

Construction of phage display libraries for expression of antibodies, particularly the Fab portion of antibodies, is well known in the art. Preferably, the phage display antibody libraries that express antibodies are prepared according to the methods described in U.S. Pat. No. 5,223,409, issued Jun. 29, 1993 and U.S. patent application Ser. No. 07/945, 515, filed Sep. 16, 1992, incorporated herein by reference. Procedures of the general methodology can be adapted using the present disclosure to produce antibodies of the present invention.

Isolation of RNA Encoding Prion-specific Antibodies

In general, the phage display anti-PrP antibody libraries are prepared by first isolating a pool of RNA that contains RNA encoding anti-PrP antibodies. To accomplish this, an animal (e.g., a mouse, rat, or hamster) is immunized with prion of interest. However, normal animals do not produce antibodies to prions at detectable or satisfactorily high levels. This problem is avoided by immunizing animals in which the (PrP) gene has been ablated on both alleles. Such mice are designated $Prnp^{0/0}$ and methods for making such mice are disclosed in Büeler, *Nature* (1992) and in Weismann Publication WO 93/10227, published May 27, 1993. Inoculation of "null" animals with prions results in production of IgG serum titers against the prion (Prusiner et al. PNAS 1993). In one preferred embodiment, the animal selected for immunization is a $Prnp^{0/0}$ mouse described by Bueler and Weismann.

Generally, the amount of prion necessary to elicit a serum antibody response in a "null" animal is from about 0.01 mg/kg to about 500 mg/kg.

The prion protein is generally administered to the animal by injection, preferably by intraperitoneal or intravenous injection, more preferably by intraperitoneal injection. The animals are injected once, with at least 1 to 4 subsequent booster injections, preferably at least 3 booster injections. After immunization, the reactivity of the animal's antisera with the prion can be tested using standard immunological assays, such as ELISA or Western blot, according to methods well known in the art (see, for example, Harlow and Lane, 1988, *Antibodies: A Laboratory Manual,* Cold Spring Harbor Laboratory Press, Cold Spring Harbor, N.Y.). Animals having prion-binding antisera may be boosted with an additional injection of prion.

Serum antibody levels are predictive of antibody secretion, and therefore of levels of specific mRNA in lymphocytes, particularly plasma cells. Detection of serum antibodies, particularly relatively high levels of serum antibodies, is thus correlated to a high level of lymphocytes such as plasma cells producing mRNA encoding those serum antibodies. Thus, plasma cells isolated from the prion protein-immunized mice will contain a high proportion of lymphocytes (e.g., plasma cells) producing prion-specific antibody, particularly when the plasma cells are isolated from the mice within a short time period after the final injection boost (e.g., about 2 to 5 days, preferably 3 days). Immunization of the mice and the subsequent injection boosters thus serve to increase the total percentage of anti-PrP antibody-producing plasma cells present in the total population of the mouse's plasma cells. Moreover, because the anti-PrP antibodies are being produced at or near peak serum levels, then anti-PrP antibody-producing plasma cells are producing anti-PrP antibodies, and thus mRNA encoding these antibodies at or near peak levels.

The above correlation between serum levels of antigen-specific antibodies, the number of lymphocytes producing those antigen-specific antibodies, and the amount of total mRNA encoding the antigen-specific antibodies provides a means for isolating a pool of mRNA that is enriched for the mRNA encoding antigen-specific antibodies of interest. Lymphocytes, including plasma cells are isolated from spleen and/or bone marrow from the prion-immunized animals according to methods well known in the art (see, for example, Huse et al. *Science* 1989). Preferably the lymphocytes are isolated about 2 to 5 days, preferably about 3 days after the final immunization boost. The total RNA is then extracted from these cells. Methods for RNA isolation from mammalian cells are well known in the art (see, for example, Sambrook et al., 1989, *Molecular Cloning: A Laboratory Manual,* 2nd Ed., Cold Spring Harbor Laboratory Press, Cold Spring Harbor, N.Y.)

Production of cDNA Encoding Antibodies from Lymphocyte mRNA cDNA is produced from the isolated RNA using reverse transcriptase according to methods well known in the art (see, for example, Sambrook et al., supra), and cDNA encoding antibody heavy chains or light chains is amplified using the polymerase chain reaction (PCR). The 3' primers used to amplify heavy chain or light chain-encoding cDNAs are based upon the known nucleotide sequences common to heavy chain or light chain antibodies of a specific antibody subclass. For example, one set of primers based upon the constant region of the IgG1 heavy chain-encoding gene can be used to amplify heavy chains of the IgG1 subclass, while another set of primers based upon the constant portion of the IgG1 light chain-encoding gene is used to amplify the light chains of the IgG1 subclass. The 5' primers are consensus sequences based upon examination of a large number of variable sequences in the data base. In this manner, DNA encoding all antibodies of a specific antibody class or subclass are amplified regardless of antigen-specificity of the antibodies encoded by the amplified DNA. The entire gene encoding the heavy chain or the light chain can be amplified. Alternatively, only a portion of the heavy or light chain encoding gene may be amplified, with the proviso that the product of PCR amplification encodes a heavy or light chain gene product that can associate with its corresponding heavy or light chain and function in antigen binding i.e., bind selectively to a prion protein. Preferably, the phage display product is a Fab or Fv antibody fragment.

The antibody encoding cDNA selected for amplification may encode any isotope and preferably encode a subclass of IgG. Exemplary mouse IgG subclasses include IgG1, IgG2a, IgG2b, and IgG3. The selection of the specific antibody subclass-encoding cDNA for amplification will vary according to a variety of factors, including, for example, the animal's serum antibody response to the antigen. Preferably, the antibody subclass-encoding cDNA selected for PCR amplification is that antibody subclass for which the animal produced the highest titer of antibody. For example, if the titers of serum IgG1 are higher than any other subclass of IgG detected in the serum antibody response, then cDNA encoding IgG1 is amplified from the cDNA pool.

Preferably, the heavy and light chains are amplified from the plasma cell cDNA to produce two separate amplified cDNA pools: 1) a cDNA pool containing heavy chain cDNA amplimer products, where the heavy chain is of a specific antibody subclass; and 2) a cDNA pool containing light chain cDNA amplimer products, where the light chain is of a specific antibody subclass.

Antibodies from Transgenic Animals

In addition to obtaining genetic material which encodes antibodies by infecting an animal with an antigen and thereafter extracting cells (and their DNA) responsible for antibody production it is possible to obtain the genetic material by producing a transgenic animal or by using the above described technology and transgenic animal technology in order to produce chimeric mouse/human or fully human antibodies. The technology for producing a chimeric or wholly foreign immunoglobins involves obtaining from cells of transgenic animals which have had inserted into their germ line a genetic material which encodes all or part of an immunoglobin which binds to the desired antigen. Wholly human antibodies can be produced from transgenic mice which have had inserted into their genome genetic material which encodes human antibodies. The technology for producing such antibodies from transgenic animals is described within PCT Publication No. WO 90/04036, published Apr. 19, 1990. Further, see Goodhartd, et al, *Proc. Natl. Acad. Sci.* U.S.A. Vol. 84, pages 4229–4233, June 1987 and Bucchine, et al, *Nature,* Vol. 326, pages 409–411, Mar. 26, 1987, all of which are incorporated herein by reference to disclose and describe methods of producing antibodies from transgenic animals.

Vectors for Use with Phase Display Antibody Libraries

The heavy chain-encoding cDNAs and the light chain-encoding cDNAs are then each inserted into separate expression cassettes of an appropriate vector. Preferably the vector contains a nucleotide sequence encoding and capable of expressing a fusion polypeptide containing, in the direction of amino- to carboxy-terminus, 1) a prokaryotic secretion signal domain, 2) an insertion site for DNA encoding a heterologous polypeptide (e.g., either the heavy or light chain-encoding cDNA), and in the expression cassette for the heavy chain cDNA 3) a filamentous phage membrane anchor domain.

The vector includes prokaryotic or mammalian DNA expression control sequences for expressing the fusion polypeptide, preferably prokaryotic control sequences. The DNA expression control sequences can include any expression signal for expressing a structural gene product, and can include 5' and 3' elements operatively linked to the expression cassette for expression of the heterologous polypeptide. The 5' control sequence defines a promoter for initiating transcription, and a ribosome binding site operatively linked at the 5'terminus of the upstream translatable sequence. The vector additionally includes an origin of replication for maintenance and replication in a prokaryotic cell, preferably a gram negative cell such as *E. coli*. The vector can also include genes whose expression confers a selective advantage, such as drug resistance, to a prokaryotic or eukaryotic cell transformed with the vector.

The filamentous phage membrane anchor is preferably a domain of the cpIII or cpVIII coat protein capable of associating with the matrix of a filamentous phage particle, thereby incorporating the fusion polypeptide onto the phage surface. The secretion signal is a leader peptide domain of a protein that targets the protein to the periplasmic membrane of gram negative bacteria. Such leader sequences for gram negative bacteria (such as *E. coli*) are well known in the art (see, for example, Oliver, In Neidhard, F. C. (ed.), *Escherichia coli and Salmonella typhimurium,* American Society for Microbiology, Washington, D.C., 1:56–69, 1987).

Filamentous Phage Membrane Anchors for Use in the Phase Display Vector

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane. In the page f1, gene VIII coat protein's membrane spanning region comprises the carboxy-terminal 11 residues from 41 to 52 (Ohkawa et al., *J. Biol. Chem.,* 256:9951–9958, 1981). An exemplary membrane anchor would consist of residues 26 to 40 to cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

The amino acid residue sequence of another preferred membrane anchor domain is derived from the M13 filamentous phage gene III coat protein (also designate cpIII). Gene III coat protein is present on a mature filamentous phage at one end of the phage particle with typically about 4 to 6 copies of the coat protein. Detailed descriptions of the structure of filamentous phage particles, their coat proteins, and particles assembly are found in the reviews by Rached et al., (Microbiol. Rev., 50:401–427, 1986) and Model et al. (In: The Bacteriophages: Vol. 2, R. Calendar, ed., Plenum Publishing Co., pgs. 375–456, 1988).

Preferably, the filamentous phage membrane anchor-encoding DNA is inserted 3' of the cDNA insert in the library vector such that the phage membrane anchor-encoding DNA can be easily excised and the vector relegated without disrupting the rest of the expression cassettes of the vector. Removal of the phage membrane anchor-encoding DNA from the vector, and expression of this vector in an appropriate host cell, results in the production of soluble antibody (Fab) fragments. The soluble Fab fragments retain the antigenicity of the phage-bound Fab, and thus can be used in assays and therapies in the manner that whole (non-fragmented) antibodies are used.

The vector for use with the present invention must be capable of expressing a heterodimeric receptor (such as an antibody or antibody Fab). That is, the vector must be capable of independently containing and expressing two separate CDNA inserts (e.g., the heavy chain cDNA and the light chain cDNA). Each expression cassette can include the elements described above, except that the filamentous phage anchor membrane-encoding DNA is present only in the expression cassette for the heavy chain cDNA. Thus, when the antibody or Fab is expressed on the surface of the phage, only the heavy chain polypeptide is anchored to the phage surface. The light chain is not directly bound to the phage surface, but is indirectly bound to the phage via its association with the free portion of the heavy chain polypeptide (i.e., the portion of the heavy chain that is not bound to the phage surface).

Preferably, the vector contains a sequence of nucleotides that allow for directional ligation, i.e., a polylinker. The polylinker is a region of the DNA expression vector that operatively links the upstream and downstream translatable DNA sequence for replication and transport, and provides a site or means for directional ligation of a DNA sequence into the vector. Typically, a directional polylinker is a sequence of nucleotides that defines two or more restriction endonuclease recognition sequence, or restriction sites. Upon restriction enzyme cleavage, the two sites yield cohesive termini to which a translatable DNA sequence can be ligated to the DNA expression vector. Preferably, the two cohesive termini are non-complementary and thereby permit directional insertion of the cDNA into the cassette. Polylinkers can provide one or multiple directional cloning sites, and may or may not be translated during expression of the inserted cDNA.

Preferably, the expression vector is capable of manipulating in the form of a filamentous phage particle. Such DNA expression vectors additionally contain a nucleotide sequence that defines a filamentous phage origin of replication such that the vector, upon presentation of the appropriate genetic complement, can replicate as a filamentous phage in single stranded replicative form, and can be packaged into filamentous phage particles. This feature provides the ability of the DNA expression vector to be packaged into phage particles for subsequent isolation of individual phage particles (e.g., by infection of and replication in isolated bacterial colonies).

A filamentous phage origin of replication is a region of the phage genome that defines sites for initiation of replication, termination of replication, and packaging of the replicative form produced by replications (see, for example, Rasched et al., Microbiol. Rev., 50:401–427, 1986; Horiuchi, J. Mol. Biol., 188:215–223, 1986). A preferred filamentous phage origin of replication for use in the present invention is an M13, f1, or fd phage origin of replication (Short et al., Nucl. Acids Res., 16:7583–7600, 1988). Preferred DNA expression vectors are the expression vectors pCOMB8, pCKAB8, pCOMB2-8, pCOMB3, pCKAB3, pCOMB2-3, pCOMB2-3' and pCOMB3H.

The pComb3H vector is a modified form of pComb3 in which (i) heavy and light chains are expressed from a single Lac promoter as opposed to individual promoters and (ii) heavy and light chains have two different leader sequences (pg1b and ompA) as opposed to the same leader sequence (pHB). Reference for pComb3H Wang, et al (1995) J. Mol. Biol., Inpress. The principles of pComb3H are basically the same as for pComb3.

Production of the Phage Display Antibody Library

After the heavy chain and light chain cDNAs are cloned into the expression vector, the entire library is packaged using an appropriate filamentous phage. The phage are then used to infect a phage-susceptible bacterial culture (such as a strain of E. coli), the phage allowed to replicate and lyse the cells, and the lysate isolated from the bacterial cell debris. The phage lysate contains the filamentous phage expressing on its surface the cloned heavy and light chains isolated from the immunized animal. In general, the heavy and light chains are present on the phage surface as Fab antibody fragments, with the heavy chain of the Fab being anchored to the phage surface via the filamentous phage membrane anchor portion of the fusion polypeptide. The light chain is associated with the heavy chain so as to form an antigen binding site. Method of producing chimeric antibodies are described within U.S. Pat. No. 4,816,567, issued Mar. 28, 1989 to Cabilly, et al which is incorporated herein by reference to disclose and describe such procedures. Further, See Bobrzecka, et al, Immunology Letters, 2, pages 151–155 (1980) and Konieczny, et al, Haematologia 14 (1), pages 85–91 (1981) also incorporated herein by reference.

Selection of Prion-antigen Specific Fabs from the Phase Display Antibody Library Phage expressing an antibody or Fab that specifically binds a prion antigen can be isolated using any of a variety of protocols for identification and isolation of monoclonal and/or polyclonal antibodies. Such methods include, immunoaffinity purification (e.g., binding of the phage to a columna having bound antigen) and antibody panning methods (e.g., repeated rounds of phage binding to antigen bound to a solid support for selection of phage of high binding affinity to the antigen). Preferably, the phage is selected by panning using techniques that are well known in the art.

After identification and isolation of phage expressing anti-PrP antibodies, the phage can be used to infect a bacterial culture, and single phage isolates identified. Each separate phage isolate can be again screened using one or more of the methods described above. In order to further confirm the affinity of the phage for the antigen, and/or to determine the relative affinities of the phage for the antigen, the DNA encoding the antibodies or Fabs can be isolated from the phage, and the nucleotide sequence of the heavy and light chains contained in the vector determined using methods well known in the art (see, for example, Sambrook et al., supra).

Isolation of Soluble Fabs from Phage Selected from the Phase Display Antibody Library Soluble antibodies or Fabs can be produced from a modified display the same dicistronic vector by excising the DNA encoding the filamentous phage anchor membrane that is associated with the expression cassette for the heavy chain of the antibody. Preferably, the DNA encoding the anchor membrane is flanked by convenient restriction sites that allow excision of the anchor membrane sequence without disruption of the remainder of the heavy chain expression cassette or disruption of any other portion of the expression vector. The modified vector without the anchor membrane sequence then allows for production of soluble heavy chain as well as soluble light chain following packaging and infection of bacterial cells with the modified vector.

Alternatively, where the vector contains the appropriate mammalian expression sequences the modified vector can be used to transform a eukaryotic cell (e.g., a mammalian or yeast cell, preferably a mammalian cell (e.g., Chinese hamster ovary (CHO) cells)) for expression of the Fab. Where the modified vector does not provide for eukaryotic expression, preferably the vector allows for excision of both the heavy and light chain expression cassettes as a single DNA fragments for subcloning into an appropriate vector. Numerous vectors for expression of proteins in prokaryotic and/or eukaryotic cells are commercially available and/or well known in the art (see, for example Sambrook et al., supra).

Commercial Assay

Examples 14–18 below and specifically Example 17 show the isolation of an antibody which specifically binds to $PrP^{Sc}$ without any denaturation. A sample containing PrP proteins (i.e., $PrP^C$ and $PrP^{Sc}$) can be subjected to denaturation by the use of protease K (PK) digestion. The use of such will digest $PrP^C$ but not $PrP^{Sc}$. Thus, after carrying out the digestion the sample is contacted with the antibody (e.g., R2) as per Example 17 under suitable binding conditions. Preferably, the antibody is bound to a substrate and can be positioned such that the sample can be easily contacted with the substrate material having the antibody bound thereon. If material binds to the antibodies on the substrate the presence of infectious $PrP^{Sc}$ is confirmed.

In commercial embodiments of the invention it may be desirable to use antibodies of the invention in a sandwich type assay. More particularly, the antibody of the invention may be bound to a substrate support surface. The sample to be tested is contacted with the support surface under conditions which allow for binding. Thereafter, unreacted sites are blocked and the surface is contacted with a generalized antibody which will bind to any protein thereon. The generalized antibody is linked to a detectable label. The generalized antibody with detectable label is allowed to bind to any $PrP^{Sc}$ bound to the antibodies on the support surface. If binding occurs the label can be made to become detectable such as by generating a color thereby indicating the presence of the label which indirectly indicates the presence of $PrP^{Sc}$ within the sample. The assay can detect prions ($PrP^{Sc}$) present in an amount of 1 part per million or less, even one part per billion or less. The $PrP^{Sc}$ may be present in a source selected from the group consisting of (a) a pharmaceutical formulation containing a therapeutically active component extracted from an animal source, (b) a component extracted from a human source, (c) an organ, tissue, body fluid or cells extracted from a human source, (d) a formulation selected form the group consisting of injectables, orals, creams, suppositories, and intrapulmonary delivery formulations, (e) a cosmetic, and (f) a pharmaceutically active compound extracted from a mammalian cell culture. Such source materials can also be treated to remove or neutralize $PrP^{Sc}$ protein by adding an antibody of the invention. The invention also includes a method of treating, comprising administering to a mammal in need thereof a therapeutically effective amount of an antibody which selectively binds $PrP^{Sc}$ protein which antibody is characterized by its ability to neutralize $PrP^{Sc}$ protein infectivity.

Generalized Procedure

Antibodies of the invention could be obtained by a variety of techniques. However, the general procedure involves synthesizing a library of proteins (i.e., antibodies or portions thereof) on the surface of phage. The library is then brought into contact with a composition which includes PrP proteins and in particular is a naturally occurring composition which includes $PrP^{Sc}$. The phage which bind to PrP protein are then isolated and the antibody or portion thereof which binds the PrP protein is isolated. It is desirable to determine the sequence of the genetic material encoding the antibody or portion thereof. Further, the sequence can be amplified and inserted, by itself, or with other genetic material into an appropriate vector and cell line for the production of other antibodies. For example, a sequence encoding a variable region which binds $PrP^{Sc}$ can be fused with a sequence which encodes a human constant region of an antibody producing a constant/variable construct. This construct can be amplified and inserted within a suitable vector which can be inserted within a suitable cell line for the production of humanized antibodies. Procedures such as this are described within U.S. Pat. No. 4,816,567, issued Mar. 28, 1989 to Cabilly, et al which is incorporated herein by reference to disclose and describe such procedures. Further, See Bobrzecka, et al, *Immunology Letters*, 2, pages 151–155 (1980) and Konieczny, et al, *Haematologia* 14 (1) , pages 85–91 (1981) also incorporated herein by reference.

When the genetic material encoding an antibody or portion thereof which binds a PrP protein is isolated it is possible to use that genetic material to produce other antibodies or portions thereof which have a greater affinity for binding PrP proteins. This is done by site directed mutagenesis technology or by random mutagenesis and selection. Specifically, individual codons or groups of codons within the sequence are removed or replaced with codons which encode different amino acids. Large numbers of different sequences can be generated, amplified and used to express variations of the antibody or portions thereof on the surface of additional phage.

The phage can then be used to test for the binding affinity of the antibody to PrP proteins.

The phage library can be created in a variety of different ways. In accordance with one procedure a host animal such as a mouse or rat is immunized with PrP protein and preferably immunized with $PrP^{Sc}$. The immunization may be carried out along with an adjuvant for the formation of larger amounts and types of antibodies. After allowing for sufficient time for the generation of antibodies, cells responsible for antibody production are extracted from the inoculated host mammal. RNA is isolated from the extracted cells and subjected to reverse transcription in order to produce a cDNA library. The extracted cDNA is amplified by the use of primers and inserted into an appropriate phage display vector. The vector allows the expression of antibodies or portions thereof on the phage surface. It is also possible to subject the cDNA to site directed mutagenesis prior to insertion into the display vector. Specifically, codons are removed or replaced with codons expressing different amino acids in order to create a larger library (i.e., a library of many variants) which is then expressed on the surface of the phage. Thereafter, as described above, the phage are brought into contact with the sample and phage which bind to PrP protein are isolated.

EXAMPLES

The following examples are put forth so as to provide those of ordinary skill in the art with a complete disclosure and description of how to make and use the recombinant anti-PrP antibodies and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Purification of MoPrP 27-30

Purified MoPrP 27-30 rods were prepared from the brains of clinically ill CD-1 mice inoculated with RML prions (Chandler scrapie isolate (Chandler R. L. 1961 Lancet, 1378–1379)). Prion rods were recovered from sucrose gradient fractions as previously described (Prusiner, McKinley 1983 Cell). Briefly, the fractions containing prion rods, which sediment in 48–60% (wt/vol) sucrose, were diluted 2:1 in distilled water and centrifuged at 100,000×g for 6 h at 4° C. The pellet was resuspended in water, centrifuged again, and the rods resuspended at 1 mg/ml in Ca/Mg-free phosphate buffered saline (PBS) containing 0.2% Sarcosyl. PrP 27-30 was the major protein as determined by SDS-PAGE and silver staining analysis. Protein quantitation was performed by bicinchonic acid dye binding, with a known amount of bovine serum albumin as the protein concentration standard.

Example 2

Immunization of $Prnp^{0/0}$ Mice $Prnp^{0/0}$ mice, in which both alleles of the PrP gene (Prnp) is ablated, were immunized with the purified MoPrP 27-30 rods, which were isolated as described in Example 1. $Prnp^{0/0}$ mice and methods for making this strain are well known in the art (Bueler, et al. 1992). $Prnp^{0/0}$ mice, which are indistinguishable from normal mice in their development and behavior, are resistant to scrapie following intracerebral inoculation of infectious $MoPrP^{Sc}$ (Büeler, et al. 1993 Cell; Prusiner et al. PNAS 1993), and will develop IgG serum titers against Mo—, SHa, and human PrP following immunization with relatively small quantities of purified SHaPrP 27-30 in adjuvant (Prusiner et al. PNAS 1993).

Three (3) six week old $Prnp^{0/0}$ mice were immunized by intraperitoneal injection of 100 μg of MoPrP 27-30 rods fully emulsified in complete Freund's adjuvant. Subsequently mice were boosted 2 times at 2-week intervals with incomplete Freund's adjuvant containing in the first instance 100 μg, then 50 μg of rods. Four days after the second boost, the reactivity of each mouse's serum against prion proteins was analyzed as described below in Example 3. Those mice having anti-PrP reactive antisera received a third injection boost of 50 μg prion rods in incomplete Freund's adjuvant 14 days after the second boost.

Example 3

Serum Reactivity of $Prnp^{0/0}$ Mice Immunized with MoPrP 27-30

A primary prognostic indicator for success in isolating a specific antibody from combinatorial libraries is serum antibody reactivity with the antigen(s) to be studied (Burton and Barbas, Adv. Immunol. 1994). Serum antibody levels are predictive of antibody secretion and therefore predictive of the levels of specific mRNA in plasma cells. It is this latter factor that ultimately dictates the composition of the antibody-encoding cDNA library.

Four days after the second boost, the $Prnp^{0/0}$ mice immunized with MoPrP 27-30 as described in Example 2 were bled from the tail, and the antisera stored at −20° C. for subsequent immunological analysis. The reactivity of the immunized mouse serum (IgG1, IgG2a, IgG2b and IgG3 antibody subclasses) was measured against denatured and non-denatured Mo— and SHaPrP 27-30 in ELISA. ELISA wells were coated overnight at 4° C. with 50 μl of PrP rods at 40 μg/ml in 100 mM sodium bicarbonate pH 8.6. Where denatured PrP rods were used as the antigen in the ELISA, 50 μl of 6M guanidinium isothiocyanate was added to the well for 15 min at room temperature, after which the wells were washed 6 times with Ca/Mg-free PBS. All wells were then blocked with Ca/Mg-free PBS containing 3% BSA. The antisera was serially diluted in PBS, and incubated with the wells for one hour at 37° C. Excess antisera was removed by washing 10 times with PBS 10.05% Tween 20 and bound antisera detected using labeled goat anti-mouse antibody that specifically binds either IgG1, IgG2a, IgG2b or IgG3 murine antibodies.

Figure 5:
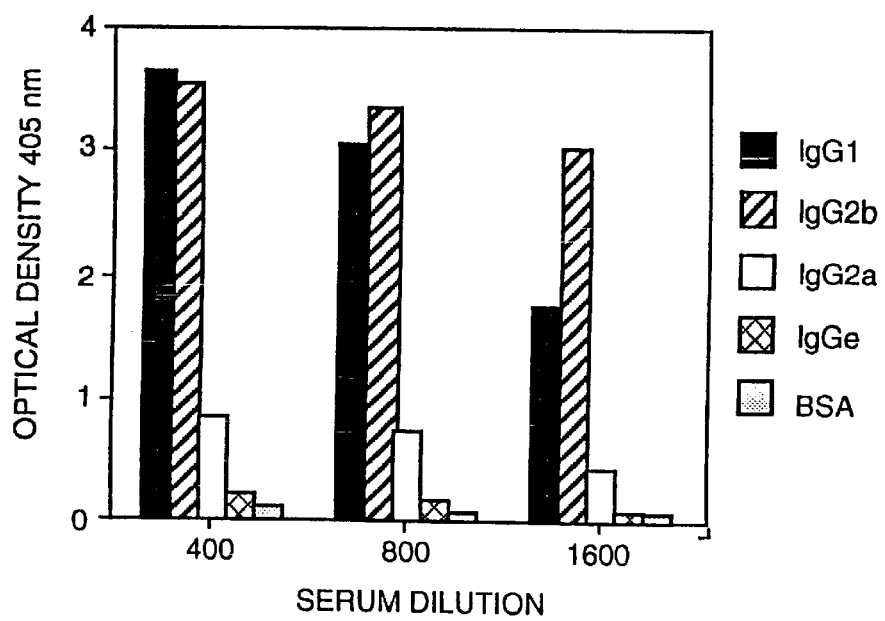
FIG. 5 is a bar graph of serum dilution vs optical density at 405 nm for the mouse (D7282) for serum against denatured mouse PrP 27-30.
Figure 8A:
FIGS. 8A–8H show photos of histoblots 8A, 8B, 8C, 8D, 8E, 8F, 8G and 8H showing staining of SHaPrP 27-30 and denatured SHaPrP 27-30.
Figure 8B:
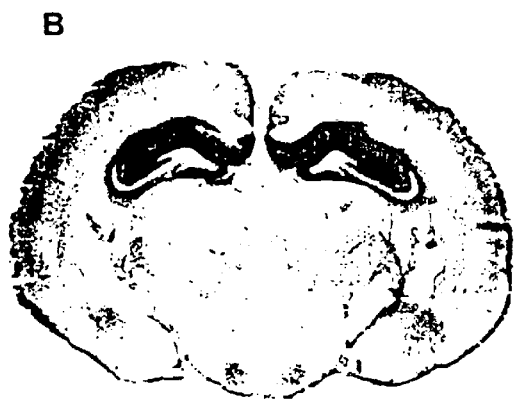
Figure 8C:
Figure 8D:
Figure 8E:
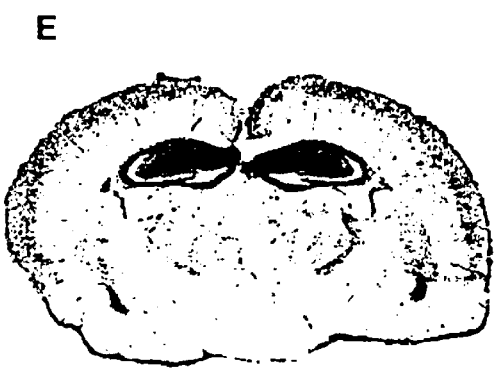
Figure 8F:
Figure 8G:
Figure 8H:

All 3 mice produced anti-PrP IgG antibodies. Serum reactivity from one of the mice, designated D7282, is illustrated in FIG. 5 as exemplary of the antibody responses of the immunized mice. The highest serum titers against Mo— and SHaPrP antigens were of the IgG1 and IgG2b subclasses. In contrast, the IgG2a and IgG3 anti-PrP titers were close to the background levels of reactivity seen for all IgG subclasses in the serum of non-immunized $Prnp^{0/0}$ mice. Antibody titers were greater against denatured rods than non-denatured rods. The similar serum reactivity against Mo— and SHa denatured rods is likely reflective of the high amino acid sequence homology between the two proteins. However, although there was considerable serum reactivity against non-denatured Mo— rods (approximately 40–50% of the level of that for denatured MoPrP 27-30), reactivity with non-denatured SHa rods was at the level of background.

Example 4

Isolation of mRNA Encoding Anti-PrP Antibodies and Construction of Antibody Phage Display Libraries Three days after the final injection boost, the D7282 mouse was sacrificed and RNA prepared from bone marrow and splenic tissues. Total RNA from mouse spleen was prepared according to methods well known in the art (Huse, et al Science 1989). RNA was prepared from bone marrow tissues by first removing the tibia and fibula from both rear legs of the mice. The bones were then cut through close to each end, and their contents flushed out by injection of guanidinium isothiocyanate into the bone cavity using a 27 gauge needle. RNA preparation was then continued as described for the mouse spleen.

The RNA preparations were then pooled, and cDNA generated from the mRNA using reverse transcriptase according to methods well known in the art. Two cDNA libraries were independently constructed from the D7282 mouse mRNA: 1) an IgG1 library; and 2) a IgG2b library. For each of these libraries, cDNAs encoding heavy chains and cDNA light chains were separately amplified by PCR from separate fractions of the pooled cDNA. The oligonucleotide 5' and 3' primers employed for PCR amplification of DNA fragments encoding murine light (κ) chains and heavy (α1 or α2b) chains of the IgG1 subclass wee those used by Huse, et al (Science 1989) and additional heavy chain primers as presented in Table 1 and heavy chain polymers which are presented in Table 1. Primers used for amplification of cDNAs encoding heavy chain fragments.

IgG1 or IgG2b phage display library is constructed by inserting the amplified cDNA encoding IgG1 or IgG2b heavy chain and the amplified cDNA encoding light chain into the pComb3H vector such that each vector contains a cDNA insert encoding a heavy chain fragment in one expression cassette of the vector, and a cDNA insert encoding a light chain fragment into the other expression cassette of the vector. The resulting IgG1 library contained approximately $9 \times 10^6$ individual clones, while the resulting IgG2b library contained approximately $7 \times 10^6$ individual clones.

The ligated vectors were then packaged by the filamentous phage M13 using methods well known in the art (see, for example, Sambrook et al, supra). The packaged library is then used to infect a culture of *E. coli,* so as to amplify the number of phage particles. After bacterial cell lysis, the phage particles are isolated and used in the panning procedure that follows. Aliquots of the phage library are stored for future amplification and use. Separate aliquots of the phage libraries are isolated and stored for future amplification and use.

TABLE 1

HEAVY CHAIN PRIMERS

```
Primer                    Nucleotide Sequence

MVH 1b (SEQ ID NOS:5, 6)  5'-[CG]AG GTG CAG CTC GAG.GAG TCA GGA CCT-3'
MVH 2b (SEQ ID NO:7)      5'-GAG GTC CAG CTC GAG CAG TCT GGA CCT-3'
MVH 3b (SEQ ID NO:8)      5'-CAG GTC CAA CTC CAA CTC GAG CAG CCT GGG GTC-3'
MVH 4b (SEQ ID NO:9       5'-GAG GTT CAG CTC GAG CAG TCT GGG GCAA-3'
MVH 5b (SEQ ID NO:10, 11) 5'-GA[Ag]GTG AAG CTC GAG GAG TCT GGA GGA-3'
MVH 6b (SEQ ID NO:12)     5'-GAG GTG AAG CTT CTC GAG TCT GGA GGT-3'
MVH 7b (SEQ ID NO:13)     5'-GAA GTG AAG CTC GAG GAG TCT GGG GGA-3'
MVH 8b (SEQ ID NO:14)     5'-GAG GTT CAG CTC GAG GAG CAG TCT GGA GCT-3'
MVH 1a (SEQ ID NO:15-46   5'-AGG T[CG][CA] A[GA]C T[GT]C TCG AGT C[TA]GG-3'
MVH 2a (SEQ ID NO:47)     5'-AGG TCC AGC TGC TCG AGT CTG G-3'
MVH 3a (SEQ ID NO:48)     5'-AGG TCC AGC TGC TCG AGT CAG G-3'
MVH 4a (SEQ ID NO:49)     5'-AGG TCC AGC TTC TCG AGT CTG G-3'
MVH 5a (SEQ ID NO:50)     5'-AGG TCC AGC TTC TCG AGT CAG G-3'
                          Primers used for the Amplification
                          of Antibody Light Chain Fragments

5' PRIMERS

MVK 1 (SEQ ID NO:51) 5'-CCA GTT CCG AGC TCG TTG TGA CTC AGG AAT CT-3'
MVK 2 (SEQ ID NO:52) 5'-CCA GTT CCG AGC TCG TGG TGA CGC AGC CGC CC-3'
MVK 3 (SEQ ID NO:53) 5'-CCA GTT CCG AGC TCG TGC TCA CCC AGT CTC CA-3'
MVK 4 (SEQ ID NO:54) 5'-CCA GTT CCG AGC TCC AGA TGA CCC AGT CTC CA-3'
MVK 5 (SEQ ID NO:55) 5'-CCA GAT GTG AGC TCG TGA CCC AGA CTC CA-3'
MVK 6 (SEQ ID NO:56) 5'-CCA GAT GTG AGC TCG TCA TGA CCC AGT CTC CA-3'
MVK 7 (SEQ ID NO:57) 5'-CCA GTT CCG AGC TCG TGA TGA CAC AGT CTC CA-3'
3' PRIMERS

MCK 1 (SEQ ID NO:58) 5'-GCG CCG TCT AGA ATT AAC ACT CAT TCC TGT TGA A-3'
MVH 6a (SEQ ID NO:59) 5'-AGG TCC AAC TGC TCG AGT CTG G-3'
MVH 7a (SEQ ID NO:60) 5'-AGG TCC AAC TGC TCG AGT TCA G-3'
MVH 8a (SEQ ID NO:61) 5'-AGG TCC AAC TTC TCG AGT CTG G-3'
3' PRIMERS

MIgG1 (SEQ ID NO:62) 5'-AGG CTT ACT AGT ACA ATC CCT GGG CAC AAT-3'
MIgG2B (SEQ ID NO:63) 5'-CTC CTT ACT AGT AGG ACA GGG GAT TGT-3'
```

PCR was performed using a Perkin Elmer 9600 with 35 rounds of amplification; denaturation at 94° C. for 30 sec, hybridization at 52° C. for 60 sec and extension at 72° C. for 60 sec.

The resulting amplified cDNAs encoding heavy chains of the IgG1 and IgG2b subclasses and light chains were cloned into the vector pComb3. The preparation of Fab antibody libraries displayed on the surface of a filamentous phage using the pComb3 vector have been described (Williamson et al. PNAS, 1993; Barbas et al. PNAS 1991). Briefly, the Example 5

Screening of the Phage Display Antibody Library for Binding to PrP

Antigen binding phage were selected for binding to denatured MoPrP 27-30 rods against PrP antigen bound to ELISA wells through a panning procedure described in (Burton, et al PNAS 1991, Barbas Lerner Methods in Enzymol 1991). Briefly, ELISA wells were coated overnight at 40° C. with 50 μl of MoPrP 27-30 rods at 40 μg/ml in 100 mM sodium bicarbonate pH 8.6. The PrP rods were then denatured by incubation with 50 µl of 6M guanidinium isothiocyanate for 15 min at room temperature, after which the wells were washed 6 times with Ca/Mg-free PBS. The wells were then blocked with Ca/Mg-free PBS containing 3% BSA.

Aliquots of antibody phage were applied to separate PrP coated ELISA wells. A total of approximately 1×10$^{10}$ antibody phage were added per well in the panning experiment.

The phage were incubated with the well-bound MoPrP antigen for 2 hrs at 37° C. Unbound phage were removed by washing 10 times with PBS 0.5% TWEEN 20. Bound phage were then removed from the wells by acid elution, pooled, reamplified and subjected to a second round of panning.

The IgG1 library was selected through 5 rounds of panning. A 40-fold amplification of PrP-specific antibody phage, as determined by the number of phage eluted from PrP-coated ELISA wells, was measured from the first to the fifth round.

Example 6

Soluble Fab Production from Selected Antibody-producing Phase

Soluble Fabs were produced from phage clones eluted from the fourth and fifth rounds of panning. DNA from the selected phage clones was isolated, and the phage coat protein III (the filamentous phage membrane anchor) was removed from the pComb3H vector using the appropriate restriction enzymes. The DNA was self-ligated to yield a vector capable of expressing soluble Fab (the procedure for production of soluble Fabs is detailed in (Barbas et al. PNAS 1991)). The vectors were then separately used to transform bacteria for expression of the Fabs, and isolated transformants were selected.

Fab expression was induced in an overnight bacterial culture using isopropyl β-D-thiogalactopyranoside. The bacteria were centrifuged, and the resulting bacterial pellet was either sonicated or frozen and thawed three times to release Fab from the bacterial periplasmic space. The bacterial Fab supernatants were then tested for reactivity against PrP in ELISA.

Example 7

ELISA Analysis of Anti-PrP Fabs Binding to PrP Antigens

The binding of soluble Fabs produced in Example 6 to denatured and non-denatured PrP antigens as well as to synthetic PrP peptides was determined using the ELISA assay described in Example 3. Synthetic PrP peptides were produced using conventional peptide synthesis protocols well known in the art.

Of the Fab clones taken from the fourth round of the panning against denatured MoPrP rods, less than 5% were reactive with denatured PrP, while approximately 50% of the clones taken from the fifth round of the same panning recognized PrP antigens. In ELISA all of the reactive clones from this panning were able to bind specifically to denatured Mo and SHa rods, but not to non-denatured rods from either species. In addition, all the anti-PrP Fabs failed to recognize synthetic peptides spanning residues 90–145 of Mo and SHa PrP, suggesting the antibodies bind between residues 146 and 2:31 of the prion protein.

Example 8

Analysis of Selected Anti-PrP Antibody (Fab) Binding to Prion-infected and Uninfected Rodent Brain Tissue The reactivity of the antibodies identified by panning of the phage display antibody library was tested by SDS/PAGE of prion-infected rodent brain tissue and Western blot analysis using the selected Fabs. Protein from brain tissues of prion-infected and uninfected mice was used as the antigen against which immunoreactivity was tested. The antigen was prepared by disrupting rodent brain tissue in Ca/Mg-free PBS by passage 5 times through a 20 gauge needle, followed by passage 10 times through a 22 gauge needle. The 10% (wt/vol) homogenate was then centrifuged at 1600×g for 5 min at 4° C. Aliquots of the supernatant protein were diluted to a final concentration of 1 mg/ml in Ca/Mg-free PBS containing 0.2% Sarcosyl. This dilution was mixed with an equal volume of non-reducing 2×SDS/PAGE sample buffer and boiled for 5 min, before SDS/PAGE (Laemmli. U.K. (1970) Nature (London) 227, 680–685). Immunoblotting was performed as previously described (Pan et al, PNAS 1993) with primary mouse IgG antiserum (Pierce) diluted 1:1000.

Example 9

Nucleic Acid Sequencing

The nucleotide and amino acid sequences of the variable domains of the antibody light and heavy chains were determined for several of the PrP specific clones. Nucleic acid sequencing was performed with a model 373A automated DNA sequencer (Applied Biosystems) using a Taq fluorescent dideoxynucleotide terminator cycle sequencing kit (Applied Biosystems). Primers for the elucidation of antibody light-chain sequence were primers MoSeqKb (SEQ ID NO: 64) [5'-CAC GAC TGA GGC ACC TCC-3'] and OmpSeq (SEQ ID NO: 65) [5'-AAG ACA GCT ATC GCG ATT GCA G-3'] hybridizing to the (−)-strand and for the heavy chain MOIgGGzSeq (SEQ ID NO: 66) [5'-ATA GCC CTT GAC CAG GCA TCC CAG GGT CAC-3'] binding to the (+)-strand and PelSeq (SEQ ID NO: 67) (5'-ACC TAT TGC CTA CGG CAG CCG-3'] binding to the (−)-strand.

The deduced amino acid sequences for some of the phage clones obtained in one panning against: denatured PrP are provided in FIGS. 6 (SEQ ID NOS: 68–74) and (SEQ ID NOS: 75–86) 7. FIG. 6 shows the amino acid sequences of selected (A) heavy chain and (B) light chain variable regions generated by panning an IgG1 library from mouse D7282 against denatured MoPrP 27-30 rods. The sequences are very similar but contain a number of heterogeneities which are likely the result of somatic mutation following repeated exposure of the mouse to PrP antigen. All of the heavy chain sequences examined in these clones contained very similar sequences. In particular, the heavy chain complementarity determining region 3(HCDR3) was identical at the nucleotide level in all the Fab clones examined. Small differences were observed in the CDR1,, CDR2, framework (FR) 3 and FR4 of the heavy chain. These differences are too numerous to be attributable to PCR or sequencing errors and have probably accrued during rounds of somatic mutation as the mouse was repeatedly boosted with antigen. The light chain sequences were also very similar, but with localized heterogeneity throughout the variable domain, again probably resultant of somatic mutation.

Example 10

Selection of Anti-prion Antibodies Following Masking of Epitopes with Existing Antibodies Panning of the IgG1 library against denatured PrP produced a series of related antibodies, presumably somatic variants of a clone directed to a single epitope (Example 9).

To access antibodies to other epitopes, a prototype antibody from the above series was added to denatured PrP in ELISA wells prior to panning in the normal way. The masking antibody was used in all subsequent panning steps. Using this procedure, antibodies were derived of different sequence which reacted with denatured PrP in ELISA. These antibodies are likely directed to different epitopes on PrP. The masking procedure was carried out as described in Ditzel, et al (1995) J. Immunol. Masking could also be carried out with molecules other than antibodies which interacted with PrP.

Example 11

Selection of Phage Particles Expressing Anti-PrP Antibodies Specific for PrP$^{Sc}$ A phage display antibody library similar to that described in the Examples above is subjected to panning experiments to identify phage clones that bind to PrP$^{Sc}$, but not to PrP$^C$. PrP$^{Sc}$ asntigen and PrP$^C$ antigen are bound to separate wells of a microtiter dish as described above for the ELISA assay. The phage display antibody library is first panned over the PrP$^C$ ELISA wells. Unbound phage are retrieved from the wells and pooled. Phage that binds to the PrP$^C$ antigen are removed from the wells and either discarded or pooled for later analyses. The pooled unbound phage are then again added to PrP$^C$ ELISA wells, with selection again being based upon lack of binding to the PrP$^c$. After several repeated selections on the PrP$^C$ antigen, the phage are pooled and panned on the ELISA wells containing the PrP$^{Sc}$ antigen. The panning is repeated for several rounds, with the phage that binds to the PrP$^{Sc}$ antigen being the phage that is selected for further rounds of panning. After 5 to 10 rounds of panning on the PrP$^{Sc}$ antigen, the phage are isolated one from another. The ability of the PrP$^{Sc}$-specific phage or isolated Fab to bind PrP$^C$ antigen can be double-checked by ELISA with the PrP$^C$ antigen. The resulting selected phage are those that bind PrP$^{Sc}$, but do not bind PrP$^C$.

Example 12

Selection of Phage Particles Expressing Anti-PrP Antibodies to Identify PrP$^{Sc}$ Regardless of Isoform A phage display antibody library is prepared as described above from lymphocyte RNA from a mouse immunized with several PrP$^{Sc}$ isoforms, or from a pool of lymphocyte RNA from several mice immunized with different PrP$^{Sc}$ isoforms. The phage are then panned with several different wells containing antigens from different isoforms of PrP$^{Sc}$. The phage are panned over each PrP$^{Sc}$ isoform with the selection being for phage that bind the isoform at each stage. The phage are panned for a total of about 5 to 10 rounds on each PrP$^{Sc}$ isoform. The phage that remain after all stages of panning against all the isoforms tested are then isolated. The immunoreactivity of each selected phage or isolated Fab is tested by ELISA or Western blot or histochemistry against each of the various PrP$^{Sc}$ isoforms, as well as for cross-reactivity with PrP$^C$.

Example 13

Selection of Phage Particles Expressing Anti-PrP Antibodies Specific for Isoforms of PrP$^{Sc}$ A phage display antibody library prepared from lymphocyte RNA of a mouse immunized with a specific PrP$^{Sc}$ isoform is prepared according to the Examples above. The resulting phage are then selected for their ability to bind only one specific PrP$^{Sc}$ isoform by panning. The panning uses several different wells containing antigens from different isoforms of PrP$^{Sc}$, including one set of wells containing antigens from the specific PrP$^{Sc}$ isoform against which specific antibodies are desired. The phage are first panned over the undesirable PrP$^{Sc}$ isoforms, with the selection being for phage that do not bind the antigen. Panning continues for a total of about 5 to 10 rounds on each of the PrP$^{Sc}$ isoforms. The phage that did not bind the undesirable PrP$^{Sc}$ isoforms are then panned for about 5 to 10 rounds against the desirable PrP$^{Sc}$ isoform, with selection for antigen binding. The phage that remain after all rounds of panning are isolated. These selected phage are those that express antibodies with binding specificity for only the specific PrP$^{Sc}$ isoform desired. The immunoreactivity of each selected phage or isolated Fab is tested by ELISA or Western blot against each of the various PrP$^{Sc}$ isoforms, as well as for cross-reactivity with PrP$^C$.

Example 14

Generation and Characterization of Serum Reactivity Against PrP$^{Sc}$ In PrP Mice Experimentation per the above Examples established that the primary prognostic indicator for success in isolating a specific antibody from combinatorial libraries with the size range of $10^7$ pfu/ml is the serum reactivity with the antigen to be studied, and it is this factor which will ultimately dictate the composition of the library. Although Prnp$^{o/o}$ mice elucidated a strong immune response upon immunization with either mouse (Mo) or Syrian hamster (SHa) prion rods composed of PrP 27-30 proteins, the highest serum titers were seen in the IgG1 and IgG2b subclasses. The IgG2a and IgG3 anti-PrP titers were close to the background levels of reactivity seen for all IgG subclasses in the serum of non-immunized mice. In an attempt to increase the immune response and augment the immune repertoire against PrP$^{Sc}$, Prnp$^{o/o}$ (94% FVB) female mice were immunized with liposomes containing SHaPrP 27-30. To further increase the immune response diversity, mice were immunized using both short and long term protocols. In contrast to immunization with SHa prion rods immunization with liposomes containing SHaPrP 27-30 resulted in antiserum titer which includes all four IgG subclasses.

Example 15

PrP-immunized Sera Reactivity Against Histoblots

To further investigate the properties of the IgG anti-SHaPrP 27-30 found in the sera from mice immunized with liposomes containing SHaPrP 27-30, we tested the sera in situ with histoblotting techniques, in which cryostat sections of normal and scrapie infected SHa brain were transferred onto nitrocellulose membranes. Although both sera showed some nonspecific reactivity against proteinase K (PK)-treated normal SHa brain sections, only the sera from the long term immunized mice showed increased reactivity against PK-treated SHa scrapie infected brain sections. This reactivity was also evident in sera dilution to 1/1000 (results not shown). Both sera showed typical reactivity against SHa scrapie infected brain sections which were first PK-treated and then exposed to 3M GdnSCN for 10 minutes. Sera from non-immunized Prnp$^{o/o}$ (94% FVB) female mice did not show any immune reactivity against normal scrapie infected SHa brain sections.

Staining of SHaPrP 27-30 and Denatured SHaPrP 27-30 in Histoblots of Scrapie Infected SHa Brain Histoblots were treated with proteinase K to remove PrP$^C$ from the brain of normal, uninoculated control SHa and SHa showing clinical signs of scrapie following inoculation with Sc237 prions. To denature SHaPrP 27-30, histoblots were treated with 3M GdnSCN for 10 minutes. Blots were incubated overnight at 4° C. with sera diluted 1/200 from the short and the long term immunized mice. The results described here show clear positive reactivity of an antiserum with non-denatured infectious prions i.e., native PrP$^{Sc}$.

FIG. 8 shows eight different stained histoblots of scrapie infected SHa brain. The histoblots were treated with proteinase K to remove PrP$^C$ from the brain of normal, non-inoculated control SHa(A, C, E and G) and SHa showing clinical signs of scrapie following inoculation with Sc 237 prions (B, D, F and H). To denature the SHaPrP 27-30, the histoblots were treated with 3M GdnSCN for 10 minutes (C, D, G and H). The blots were incubated overnight at 4° C with sera diluted 1/200 from the short (A-D) and the long (E-H) term immunized mice. The results clearly show the ability of the antibodies of the invention to bind to native, non-denatured infectious prions i.e., bind to native PrP$^{Sc}$.

Example 16

Generation of Monoclonal Antibodies from Immunized Mice of Example 14

Overall, eight phage Fab display libraries were constructed: IgG1k, IgG2ak, IgG2bk and IgG3k from mRNA extracted from the short and long term immunized mice. To overcome difficulties with the isolation of phage expressing anti-PrP Fab by panning against prion rods containing PrP 27-30, a panning system was used where libraries are panned against biotinylated SHa 27-30, dispersed into liposomes, and bound to streptavidin-coated microtiter plates. After five rounds of panning, *E. Coli* extracts from more than 50 clones reacted with biotinylated SHa 27-30, SHa 27-30 rods and 90–231 recombinant SHa in ELISA. Since these clones also react with recombinant rPrP corresponding to SHaPrP residues 90–231, Melhorn, I., et al, High-level Expression and Characterization of a Purified 142-residue Polypeptide of the Prion Protein. *Biochemistry* 35, 5528–2237 (1996), all eight libraries were panned against this antigen to successfully isolate more distinct clones from virtually all the libraries. Upon DNA sequencing of the plasmid region coding for the IgG heavy chain, 30 Fabs were identified as distinct clones.

Example 17

Characterization of Monoclonal Antibodies

Initial ELISA with *E. Coli* extracts from positive clones suggested that the Fabs, in contrast to the monoclonal 3F4 antibody, Kascsak, R. J., et al, Mouse Polyclonal and Monoclonal Antibody to Scrapie Associated Fibril Proteins, *J. Virol.* 61, 3688–3693 (1987), bind to PrP 27-30 in a native state, i.e., without a denaturation step. To characterize quantitatively the novelty of these Fabs, we purified them and produced 3F4 Fab from the monoclonal 3F4 by enzymatic cleavage. Standard ELISA for the detection of SHaPrP was performed using different concentrations of the purified Fabs. In contrast to 3F4 which showed characteristic SHa PrP binding properties (basal binding to prion rods and strong reactivity against SHaPrP 27-30 after treatment with 3M non-denaturant GdnSCN), the newly isolated Fabs reacted against prion rods without any denaturation step.

The half-maximal binding to non-denatured prion rods occurs at a Fab concentration of approximately 0.5 pg/ml, indicating that the antibody has an apparent binding affinity of approximately $10^8$ moles/liter.

Figure 9:
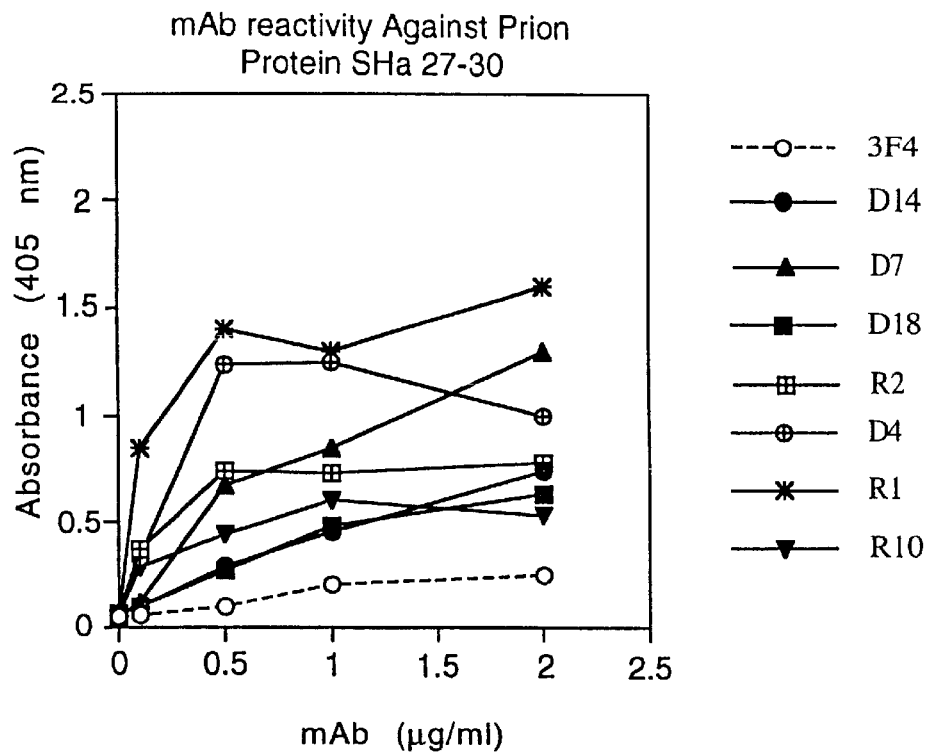
FIG. 9 is a graph showing the ELISA reactivity of purified Fabs against prion protein SHa 27-30.

FIG. 9 is a graph showing the ELISA reactivity of purified Fabs against prion protein SHa 27-30. The antibody 3F4 and recombinant antibodies were examined at different concentrations for binding to ELISA wells which were coated with 0.2 µ/g of sucrose purified infectious SHa prion rods. The results clearly show that all of the recombinant antibodies of the invention have substantially higher degrees of binding to prions as compared to the antibody 3F4.

Protocol For ELISA Reactivity of Purified Fabs Against Denatured Prion Protein SHa 27-30

Purified 3F4 Fab and recombinant Fabs were examined at different concentrations for binding to ELISA wells coated with 0.2 µg of sucrose purified SHa prion rods either native or denatured in the ELISA well with 3M GdnSCN for 10 min.

Figure 10:
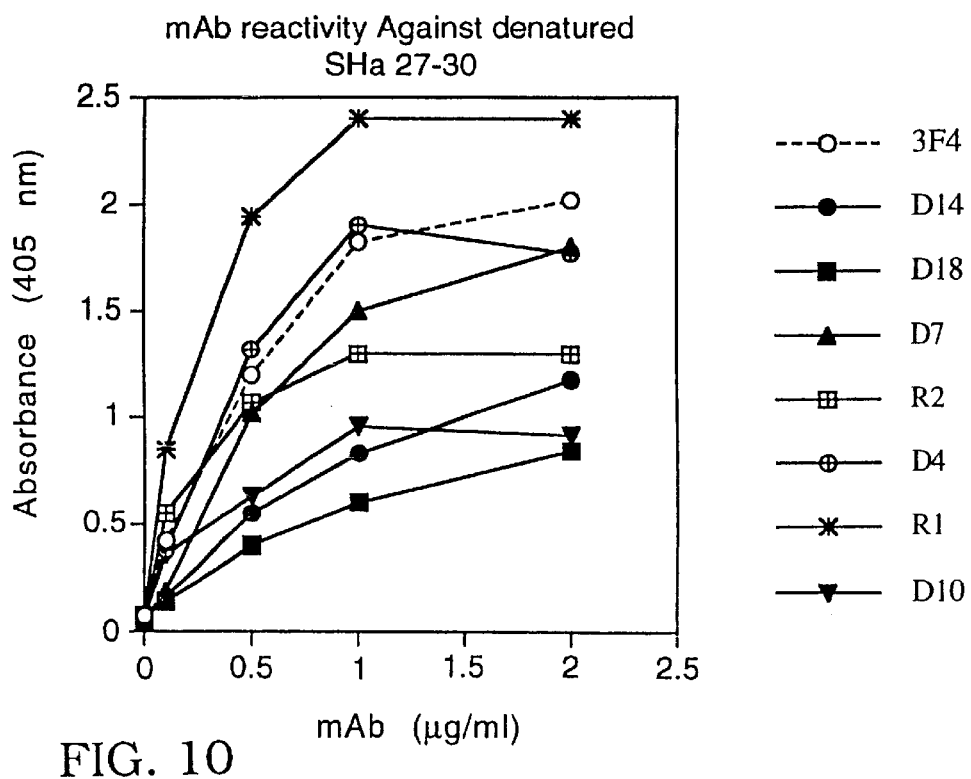
FIG. 10 is a graph of the ELISA Reactivity of purified Fabs against denatured prion protein SHa 27-30.

FIG. 10 is a graph showing the results of ELISA reactivity purified Fabs against denatured prion protein SHa 27-30. FIG. 10 is interesting as compared to FIG. 9 in that the recombinant antibodies of the invention as per FIG. 9 show a higher degree of affinity for the prion rods as compared to 3F4 whereas all of the recombinant antibodies but for R1 show a lower degree of affinity against denatured antigen.

Example 18

Characterization of Monoclonal Antibody by Immunoprecipitation

Immunoprecipitation of SHaPrP 27-30

To confirm the anti-PrP 27-30 activity of the Fabs as well as to confirm the in-ability of 3F4 to bind nondenatured SHaPrP 27-30, an immunoprecipitation method was developed using liposomes containing SHa 27-30. *E. Coli* extracts from Fab producing clones immunoprecipitated 40–50% of the SHaPrP 27-30 present in the solution, while 3F4 in dilution of 1/500 immunoprecipitated only trace amounts of SHaPrP. Fab concentrations in bacterial supernates are typically on the order of 1–10 pg/ml. This implies that the affinity for antigen are high (on the order of $10^7$–$10^8$ moles/liter or more). The antibody 3F4 was obtained as an ascetic fluid and is expected to have a concentration of approximately 1 µg/ml at the dilution used in the immunoprecipitation experiment. The ability of the new Fabs to immunoprecipitate SHaPrP 27-30 in comparison to 3F4 was determined quantitatively with purified Fab mabs D4 and R2. Fab 2R immunoprecipitated SHaPrP 27-30 strongly at concentrations as low as 0.1 pg/ml (50 ng in 500 pl) indicating an affinity on the order of greater than $10^8 M^{-1}$ (i.e., $10^8$ mole/liter). Fab 2R was less potent but clearly immune precipitated antigen more efficiently than 3F4. Note that D4, R2, 6D2, D14, R1 and R10 all refer to antibodies of the invention.

Immunoprecipitation of SHaPrP 27-30 with Recombinant Fabs

The ability of 3F4 diluted 1/500 and 100 µl of *E. Coli* extracts containing Fab to immunoprecipitate SHaPrP 27-30 was monitored by western blotting. All lanes except lane 14 are from immunoprecipitations containing goat anti-mouse IgG Fab and protein A agarose. 10 µl of liposomes containing SHa PrP 27-30 were added to lanes 1, 3, 5, 7, 9, 11, 13. 100 µl of *E. Coli* extracts from different clones diluted 1/500 were added as follows: lanes 2–3, 6D2; lanes 4–5, D14; lanes 6–7, R1; lanes 8–9, R10; lanes 10–11, D4; lanes 12–13, 3F4. Lane 14 was loaded with ½ volume of liposomes used for immunoprecipitations.

The results described above are shown within the photograph of FIG. 11. The photo clearly shows higher degrees of immunoprecipitation when using the recombinant antibodies of the invention.

Figure 12:
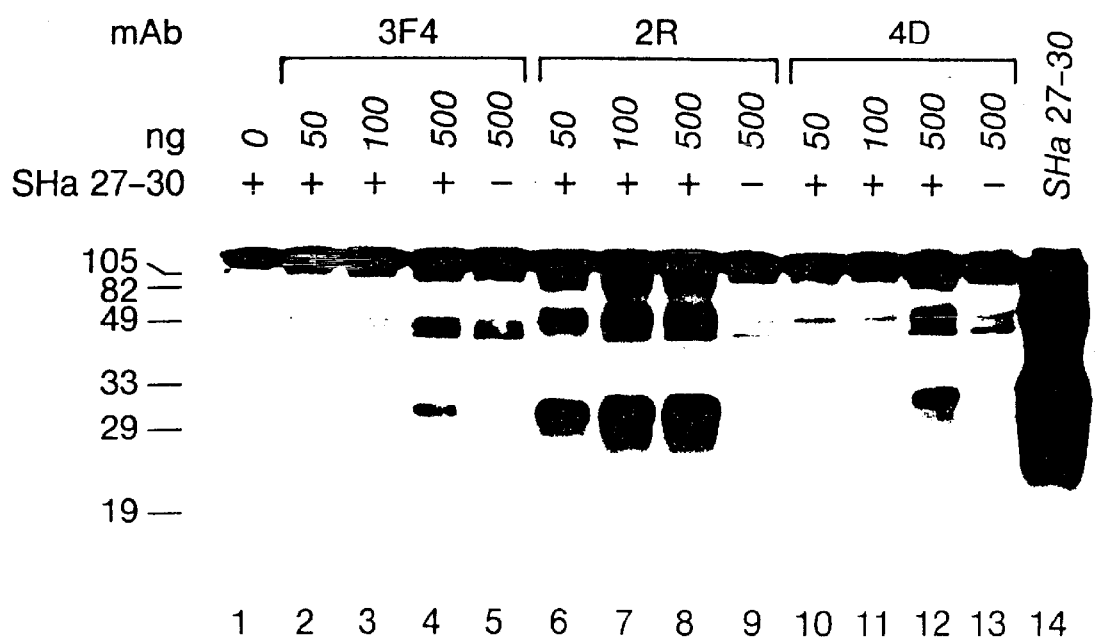
FIG. 12 is a photo showing amino precipitation of SHaPrP 27-30 with purified Fabs of the invention.

FIG. 12 is a photo showing the immunoprecipitation of SHaPrP 27-30 with purified Fabs of the invention (2R and 4D) as well as 3H4. The ability to immunoprecipitate the antigen is monitored by western blotting. All of the lanes shown in FIG. 12 but for lane 14 are immunoprecipitations containing goat anti-mouse IgG Fab and protein Agarose. To obtain the results 10 μl of liposomes containing SHaPrP 27-30 were added to all lanes except for lanes 5, 9 and 13. Each of the lanes are marked with the indicated amounts of purified Fabs (nanograms) which were added to lanes 2–13. Lane 14 was loaded with one-half volume of liposomes used for the immunoprecipitation. The results clearly show a dramatically higher degree of precipitation when using the antibodies 2R and 4D of the invention as compared to 3F4.

The ELISA data (FIG. 9) clearly show a number of Fabs with a saturable binding to non-denatured PrP 27-30 and a half-maximal binding at around 0.5 μg/ml. This corresponds to an apparent affinity constant at $10^8$ $M^{-1}$ (MW of Fab= 50,000). At the same time, 3F4 shows insignificant binding out to 2 μg/ml. Moving to denatured PrP 27-30, FIG. 10, the recombinant Fabs now bind to a higher level but with a similar apparent affinity. This suggests denaturation has revealed more antigenic sites but their affinities are the same. Significantly, 3F4 is now binding comparably to the recombinant Fabs with an apparent affinity of the order of $10^8$ $M^{-1}$. Comparison of the 3F4 data in FIGS. 9 and 10 strongly suggests the integrity of PrP 27-30 in the non-denatured form. Thus it could have been argued that the recombinant Fabs were reacting with a fraction of denatured PrP present in the PrP 27-30 preparation. The lack of reactivity of 3F4 with non-denatured PrP 27-30 coupled with its strong reactivity with denatured PrP 27-30 refutes this interpretation and strongly suggests the recombinant Fabs recognize non-denatured rods with high affinity.

Figure 11:
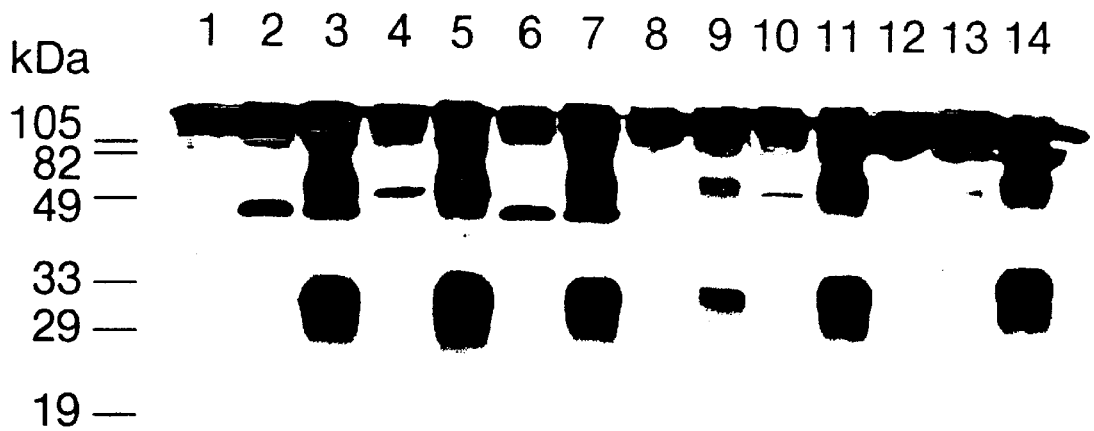
FIG. 11 is a photo showing amino precipitation of SHaPrP 27-30 with recombinant Fabs of the invention.

The immunoprecipitation data are confirmatory of the ELISA data. Low concentrations of recombinant Fabs as found in crude bacterial supernates (typically 1–10 μl/ml) are highly effective at immunoprecipitating PrP 27-30 (FIG. 11). This implies an affinity on the order of $10^7$–$10^8$ $M^{-1}$. Under comparable concentration conditions, 3F4 does not produce significant precipitation. A more quantitative analysis (FIG. 12) shows that Fab R2 immunoprecipitates PrP 27-30 highly effectively with some titration in the range 0.1–0.2 μg/ml implying a binding affinity on the order of $10^8$ $M^{-1}$. Fab 4D has a lower affinity and 3F4 immunoprecipitates very weakly indeed. From this particular experiment one could argue that the affinity of 3F4 is considerably less than $5\times10^7$ $M^{-1}$ and probably less than $10^7$ $M^{-1}$.

Overall, the data indicates that the recombinant Fabs have affinities in the range of $10^7$–$10^8$ $M^{-1}$.

The instant invention is shown and described herein in what is considered to be a most practical and preferred embodiments. It is recognized, however, that departures may be made from which are within the scope of the invention and that modifications will occur to one who is skilled in the art upon reading this disclosure.

What is claimed is:

1. A method of determining PrP$^{Sc}$ infection in a dead animal, comprising:
   extracting tissue from an animal that has died;
   contacting the tissue with an antibody characterized by its ability to bind to native PrP$^{Sc}$ in situ wherein the antibody binds to a form of PrP$^{Sc}$ specific to the animal that has died; and
   determining if the antibody has bound to PrP$^{Sc}$; wherein presence of PrP$^{Sc}$ in the tissue is indicative of PrP$^{Sc}$ infection.

2. The method of claim 1, wherein the antibody binds to native PrP$^{Sc}$ from a mammal selected from the group consisting of a human, a cow, a sheep, a horse, a pig, a dog, a chicken and a cat.

3. The method of claim 1, wherein the antibody binds to said PrP$^{Sc}$ with a binding affinity $K_a$ of $10^7$ l/mol or more.

4. The method of claim 3, wherein the $K_a$ is $10^8$ l/mol or more.

5. A method of purifying a material suspected of containing a PrP$^{Sc}$ protein, comprising:
   contacting the material with a sufficient amount of an antibody characterized by its ability to bind native PrP$^{Sc}$ in situ which antibody is bound to a support surface, and
   removing material not bound to the antibody.

6. The method of claim 5, wherein the antibody binds to native PrP$^{Sc}$ from a mammal selected from the group consisting of a human, a cow, a sheep, a horse, a pig, a dog, a chicken and a cat.

7. The method of claim 5, wherein the antibody binds to said PrP$^{Sc}$ with a binding affinity $K_a$ of $10^7$ l/mol or more.

8. The method of claim 7, wherein the $K_a$ is $10^8$ l/mol or more.

9. A method of treating a material, comprising to the material a sufficient amount of an antibody to bind native PrP$^{Sc}$ in situ.

10. The method of claim 9, wherein the antibody binds to native PrP$^{Sc}$ from a mammal selected from the group consisting of a human, a cow, a sheep, a horse, a pig, a dog, a chicken and a cat.

11. The method of claim 9, wherein the antibody binds to said PrP$^{Sc}$ with a binding affinity $K_a$ of $10^7$ l/mol or more.

12. The method of claim 11, wherein the $K_a$ is $10^8$ l/mol or more.

* * * * *

UNITED STATES PATENT AND TRADEMARK OFFICE
CERTIFICATE OF CORRECTION

PATENT NO. : 6,372,214 B1  Page 1 of 1
DATED : April 16, 2002
INVENTOR(S) : Prusiner, Stanley B. et al.

It is certified that error appears in the above-identified patent and that said Letters Patent is hereby corrected as shown below:

<u>Column 86,</u>
Line 55, after "comprising" please insert the word -- adding --.

Signed and Sealed this

Nineteenth Day of November, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
      (A) LENGTH: 254 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Thr Trp Gly Gln Pro His Gly Gly Gly Trp
        50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Gly Thr His Asn
                85                  90                  95

Gln Trp Asn Lys Pro Ser Lys Pro Lys Thr Asn Leu Lys His Val Ala
               100                 105                 110
```

```
Gly Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
        130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
        210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

(2) INFORMATION FOR SEQ ID NO:2:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
                180                 185                 190

Thr Lys Gly Glu Asn Phe Thr Glu Thr Asp Val Lys Met Met Glu Arg
        195                 200                 205
```

```
Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

(2) INFORMATION FOR SEQ ID NO:3:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
                20                  25                  30

Trp Asn Thr Gly Gly Ser Arg Tyr Pro Gly Gln Gly Ser Pro Gly Gly
            35                  40                  45

Asn Arg Tyr Pro Pro Gln Gly Gly Gly Trp Gly Gln Pro His Gly
    50                  55                  60

Gly Gly Trp Gly Gln Pro His Gly Gly Gly Trp Gly Gln Pro His Gly
65                  70                  75                  80

Gly Gly Trp Gly Gln Pro His Gly Gly Gly Trp Gly Gln Pro His Gly
                85                  90                  95

Gly Gly Gly Trp Gly Gln Gly Gly Thr His Gly Gln Trp Asn Lys Pro
                100                 105                 110

Ser Lys Pro Lys Thr Asn Met Lys His Val Ala Gly Ala Ala Ala Ala
            115                 120                 125

Gly Ala Val Val Gly Gly Leu Gly Gly Tyr Met Leu Gly Ser Ala Met
130                 135                 140

Ser Arg Pro Leu Ile His Phe Gly Ser Asp Tyr Glu Asp Arg Tyr Tyr
145                 150                 155                 160

Arg Glu Asn Met His Arg Tyr Pro Asn Gln Val Tyr Tyr Arg Pro Val
                165                 170                 175

Asp Gln Tyr Ser Asn Gln Asn Asn Phe Val His Asp Cys Val Asn Ile
            180                 185                 190

Thr Val Lys Glu His Thr Val Thr Thr Thr Thr Lys Gly Glu Asn Phe
            195                 200                 205

Thr Glu Thr Asp Ile Lys Met Met Glu Arg Val Val Glu Gln Met Cys
    210                 215                 220

Val Thr Gln Tyr Gln Lys Glu Ser Gln Ala Tyr Tyr Asp Gln Gly Ala
225                 230                 235                 240

Ser Val Ile Leu Phe Ser Ser Pro Val Ile Leu Leu Ile Ser Phe
                245                 250                 255

Leu Ile Phe Leu Ile Val Gly
                260
```

(2) INFORMATION FOR SEQ ID NO:4:

(i) SEQUENCE CHARACTERISTICS:
        (A) LENGTH: 255 amino acids

```
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:4:
```

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
                20                  25                  30

Trp Asn Thr Gly Gly Ser Arg Tyr Pro Gly Gln Gly Ser Pro Gly Gly
            35                  40                  45

Asn Arg Tyr Pro Pro Gln Gly Gly Gly Trp Gly Gln Pro His Gly
 50                  55                  60

Gly Gly Trp Gly Gln Pro His Gly Gly Trp Gly Gln Pro His Gly
 65                  70                  75                  80

Gly Ser Trp Gly Gln Pro His Gly Gly Gly Trp Gly Gln Gly Gly
                85                  90                  95

Ser His Ser Gln Trp Asn Lys Pro Ser Lys Pro Lys Thr Asn Met Lys
                100                 105                 110

His Val Ala Gly Ala Ala Ala Ala Gly Ala Val Val Gly Gly Leu Gly
                115                 120                 125

Gly Tyr Met Leu Gly Ser Ala Met Ser Arg Pro Leu Ile His Phe Gly
                130                 135                 140

Asn Asp Tyr Glu Asp Arg Tyr Tyr Arg Glu Asn Met Tyr Arg Tyr Pro
145                 150                 155                 160

Asn Gln Val Tyr Tyr Arg Pro Val Asp Gln Tyr Ser Asn Gln Asn Asn
                165                 170                 175

Phe Val His Asp Cys Val Asn Ile Thr Val Lys Gln His Thr Val Thr
                180                 185                 190

Thr Thr Thr Lys Gly Glu Asn Phe Thr Glu Thr Asp Ile Lys Ile Met
                195                 200                 205

Glu Arg Val Val Glu Gln Met Cys Ile Thr Gln Tyr Gln Arg Glu Ser
                210                 215                 220

Gln Ala Tyr Tyr Gln Arg Gly Ala Ser Val Ile Leu Phe Ser Ser Pro
225                 230                 235                 240

Pro Val Ile Leu Leu Ile Ser Phe Leu Ile Phe Leu Ile Val Gly
                245                 250                 255

```
(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAGGTGCAGC TCGAGGAGTC AGGACCT                                              27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:6:

GAGGTGCAGC TCGAGGAGTC AGGACCT                                    27

(2) INFORMATION FOR SEQ ID NO:7:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GAGGTCCAGC TCGAGCAGTC TGGACCT                                    27

(2) INFORMATION FOR SEQ ID NO:8:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CAGGTCCAAC TCGAGCAGCC TGGGGTC                                    27

(2) INFORMATION FOR SEQ ID NO:9:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

GAGGTTCAGC TCGAGCAGTC TGGGGCAA                                   28

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GAAGTGAAGC TCGAGGAGTC TGGAGGA                                    27

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

```
GAGGTGAAGC TCGAGGAGTC TGGAGGA                                27
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GAGGTGAAGC TTCTCGAGTC TGGAGGT                                27
```

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GAAGTGAAGC TCGAGGAGTC TGGGGGA                                27
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GAGGTTCAGC TCGAGGAGCA GTCTGGAGCT                             30
```

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
AGGTCCAGCT GCTCGAGTCT GG                                     22
```

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
AGGTGCAGCT GCTCGAGTCT GG                                     22
```

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGGTCAAGCT GCTCGAGTCT GG                                           22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGGTGAAGCT GCTCGAGTCT GG                                           22

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AGGTCCAACT GCTCGAGTCT GG                                           22

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AGGTGCAACT GCTCGAGTCT GG                                           22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

AGGTCAAACT GCTCGAGTCT GG                                           22

(2) INFORMATION FOR SEQ ID NO:22:

(i) SEQUENCE CHARACTERISTICS:
        (A) LENGTH: 22 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

AGGTGAAACT GCTCGAGTCT GG                                             22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

AGGTCCAGCT TCTCGAGTCT GG                                             22

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AGGTGCAGCT TCTCGAGTCT GG                                             22

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

AGGTCAAGCT TCTCGAGTCT GG                                             22

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

AGGTGAAGCT TCTCGAGTCT GG                                             22

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

AGGTCCAACT TCTCGAGTCT GG                                         22

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

AGGTGCAACT TCTCGAGTCT GG                                         22

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

AGGTCAAACT TCTCGAGTCT GG                                         22

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AGGTGAAACT TCTCGAGTCT GG                                         22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

AGGTCCAGCT GCTCGAGTCA GG                                         22

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
AGGTGCAGCT GCTCGAGTCA GG                                                22

(2) INFORMATION FOR SEQ ID NO:33:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:33:

AGGTCAAGCT GCTCGAGTCA GG                                                22

(2) INFORMATION FOR SEQ ID NO:34:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:34:

AGGTGAAGCT GCTCGAGTCA GG                                                22

(2) INFORMATION FOR SEQ ID NO:35:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:35:

AGGTCCAACT GCTCGAGTCA GG                                                22

(2) INFORMATION FOR SEQ ID NO:36:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:36:

AGGTGCAACT GCTCGAGTCA GG                                                22

(2) INFORMATION FOR SEQ ID NO:37:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:37:

AGGTCAAACT GCTCGAGTCA GG                                                22

(2) INFORMATION FOR SEQ ID NO:38:
```

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:38:

AGGTGAAACT GCTCGAGTCA GG                                    22

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

AGGTCCAGCT TCTCGAGTCA GG                                    22

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

AGGTGCAGCT TCTCGAGTCA GG                                    22

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

AGGTCAAGCT TCTCGAGTCA GG                                    22

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

AGGTGAAGCT TCTCGAGTCA GG                                    22

(2) INFORMATION FOR SEQ ID NO:43:

(i) SEQUENCE CHARACTERISTICS:
        (A) LENGTH: 22 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:43:

AGGTCCAACT TCTCGAGTCA GG                                              22

(2) INFORMATION FOR SEQ ID NO:44:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:44:

AGGTGCAACT TCTCGAGTCA GG                                              22

(2) INFORMATION FOR SEQ ID NO:45:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:45:

AGGTCAAACT TCTCGAGTCA GG                                              22

(2) INFORMATION FOR SEQ ID NO:46:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:46:

AGGTGAAACT TCTCGAGTCA GG                                              22

(2) INFORMATION FOR SEQ ID NO:47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:47:

AGGTCCAGCT GCTCGAGTCT GG                                              22

(2) INFORMATION FOR SEQ ID NO:48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:48:

AGGTCCAGCT GCTCGAGTCA GG                                                    22

(2) INFORMATION FOR SEQ ID NO:49:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:49:

AGGTCCAGCT TCTCGAGTCT GG                                                    22

(2) INFORMATION FOR SEQ ID NO:50:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:50:

AGGTCCAGCT TCTCGAGTCA GG                                                    22

(2) INFORMATION FOR SEQ ID NO:51:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:51:

CCAGTTCCGA GCTCGTTGTG ACTCAGGAAT CT                                         32

(2) INFORMATION FOR SEQ ID NO:52:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:52:

CCAGTTCCGA GCTCGTGGTG ACGCAGCCGC CC                                         32

(2) INFORMATION FOR SEQ ID NO:53:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:53:

CCAGTTCCGA GCTCGTGCTC ACCCAGTCTC CA                                         32

(2) INFORMATION FOR SEQ ID NO:54:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

CCAGTTCCGA GCTCCAGATG ACCCAGTCTC CA                        32

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

CCAGATGTGA GCTCGTGACC CAGACTCCA                           29

(2) INFORMATION FOR SEQ ID NO:56:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CCAGATGTGA GCTCGTCATG ACCCAGTCTC CA                        32

(2) INFORMATION FOR SEQ ID NO:57:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CCAGTTCCGA GCTCGTGATG ACACAGTCTC CA                        32

(2) INFORMATION FOR SEQ ID NO:58:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

GCGCCGTCTA GAATTAACAC TCATTCCTGT TGAA                      34

(2) INFORMATION FOR SEQ ID NO:59:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

AGGTCCAACT GCTCGAGTCT GG                                              22

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

AGGTCCAACT GCTCGAGTTC AG                                              22

(2) INFORMATION FOR SEQ ID NO:61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

AGGTCCAACT TCTCGAGTCT GG                                              22

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

AGGCTTACTA GTACAATCCC TGGGCACAAT                                      30

(2) INFORMATION FOR SEQ ID NO:63:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

CTCCTTACTA GTAGGACAGG GGATTGT                                         27

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO:64:

CACGACTGAG GCACCTCC                                                          18

(2) INFORMATION FOR SEQ ID NO:65:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:65:

AAGACAGCTA TCGCGATTGC AG                                                     22

(2) INFORMATION FOR SEQ ID NO:66:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:66:

ATAGCCCTTG ACCAGGCATC CCAGGGTCAC                                             30

(2) INFORMATION FOR SEQ ID NO:67:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:67:

ACCTATTGCC TACGGCAGCC G                                                      21

(2) INFORMATION FOR SEQ ID NO:68:

(i) SEQUENCE CHARACTERISTICS:
            (A) LENGTH: 114 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:68:

Leu Glu Gln Ser Gly Val Glu Leu Ala Arg Pro Gly Ala Ser Val Met
 1               5                  10                  15

Leu Ser Cys Lys Ala Ser Gly Tyr Thr Phe Thr Thr Tyr Gly Ile Ser
            20                  25                  30

Trp Val Lys Gln Arg Thr Gly Gln Gly Leu Glu Trp Ile Gly Glu Ile
        35                  40                  45

Trp Pro Arg Ser Gly Asn Thr Tyr Tyr Asn Glu Lys Phe Lys Gly Lys
    50                  55                  60

Ala Thr Leu Thr Ala Asp Lys Ser Ser Ser Thr Ala Tyr Leu Asp Leu

```
                    65                  70                  75                  80
Arg Ser Leu Thr Ser Glu Asp Ser Ala Val Tyr Phe Cys Ala Arg His
                        85                  90                  95
Asp Gly Tyr Pro Phe Ala Tyr Trp Gly Gln Gly Thr Leu Val Thr Val
                100                 105                 110
Ser Ala
```

(2) INFORMATION FOR SEQ ID NO:69:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

```
Leu Glu Gln Ser Gly Val Glu Leu Ala Arg Pro Gly Ala Ser Val Met
1                   5                   10                  15
Leu Ser Cys Lys Ala Ser Gly Tyr Thr Phe Thr Thr Tyr Gly Ile Ser
                20                  25                  30
Trp Val Lys Gln Arg Thr Gly Gln Gly Leu Glu Trp Ile Gly Glu Ile
                35                  40                  45
Cys Pro Arg Ser Gly Asn Thr Tyr Tyr Asn Glu Lys Phe Lys Gly Lys
            50                  55                  60
Ala Thr Leu Thr Ala Asp Lys Ser Ser Thr Ala Tyr Leu Asp Leu
65                  70                  75                  80
Arg Ser Leu Thr Ser Glu Asp Ser Ala Val Tyr Phe Cys Ala Arg His
                        85                  90                  95
Asp Gly Tyr Pro Phe Ala Tyr Trp Gly Gln Gly Thr Leu Val Thr Val
                100                 105                 110
Ser Ala
```

(2) INFORMATION FOR SEQ ID NO:70:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

```
Tyr Thr Phe Thr Thr Tyr Gly Ile Thr Trp Val Lys Gln Arg Thr Gly
1                   5                   10                  15
Gln Gly Leu Glu Trp Ile Gly Glu Ile Trp Pro Arg Ser Gly Asn Thr
                20                  25                  30
Tyr Tyr Asn Glu Lys Phe Lys Gly Lys Ala Thr Leu Thr Ala Asp Lys
                35                  40                  45
Ser Ser Ser Thr Ala Tyr Met Glu Val Arg Ser Leu Thr Ser Asp Asp
        50                  55                  60
Ser Ala Val Tyr Phe Cys Ala Arg His Asp Gly Tyr Pro Phe Ala Tyr
65                  70                  75                  80
Trp Gly Gln Gly Thr Leu Val Thr Val Ser Ala
                85                  90
```

(2) INFORMATION FOR SEQ ID NO:71:

(i) SEQUENCE CHARACTERISTICS:
    (A) LENGTH: 91 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:71:

```
Xaa Thr Phe Thr Val Tyr Gly Ile Ser Trp Val Lys Gln Arg Thr Gly
1               5                   10                  15

Gln Gly Leu Glu Trp Ile Gly Glu Ile Trp Pro Arg Ser Gly Asn Thr
            20                  25                  30

Tyr Tyr Asn Glu Lys Phe Lys Val Lys Ala Thr Leu Ser Ala Asp Lys
        35                  40                  45

Ser Ser Ser Thr Ala Ser Met Glu Leu Arg Ser Leu Thr Ser Glu Asp
    50                  55                  60

Ser Ala Val Tyr Phe Cys Ala Arg His Asp Gly Tyr Pro Phe Ala Tyr
65                  70                  75                  80

Trp Gly Gln Gly Thr Leu Val Thr Val Ser Ala
                85                  90
```

(2) INFORMATION FOR SEQ ID NO:72:

(i) SEQUENCE CHARACTERISTICS:
       (A) LENGTH: 95 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:72:

```
Trp Glu Xaa Arg Val Ser Leu Thr Cys Arg Ala Ser Gln Asp Phe Gly
1               5                   10                  15

Ser Ser Leu Asn Trp Phe Arg Gln Lys Pro Asp Gly Thr Ile Arg Arg
            20                  25                  30

Leu Ile Tyr Ala Thr Ser Arg Leu His Ser Gly Val Pro Lys Arg Phe
        35                  40                  45

Ser Gly Ser Arg Ser Gly Ser Asp Tyr Ser Leu Thr Ile Ser Ser Leu
    50                  55                  60

Glu Ala Glu Asp Phe Gly Asp Tyr Tyr Cys Leu Gln Tyr Ala Ala Ser
65                  70                  75                  80

Pro Phe Thr Phe Gly Ser Gly Thr Lys Leu Glu Ile Lys Arg Ala
                85                  90                  95
```

(2) INFORMATION FOR SEQ ID NO:73:

(i) SEQUENCE CHARACTERISTICS:
       (A) LENGTH: 109 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:73:

```
Glu Leu Val Met Thr Gln Thr Pro Ser Ser Leu Ser Ala Ser Leu Gly
1               5                   10                  15

Glu Arg Val Ser Leu Thr Cys Arg Ala Ser Gln Asp Phe Gly Ser Ser
            20                  25                  30
```

```
Leu Asn Trp Phe Arg Gln Ala Pro Asp Gly Thr Ile Arg Arg Leu Ile
        35                  40                  45

Tyr Ala Thr Ser Lys Leu His Ser Gly Val Pro Lys Arg Phe Ser Gly
    50                  55                  60

Ser Arg Ser Gly Ser Asp His Ser Leu Thr Ile Ser Ser Leu Glu Pro
65                  70                  75                  80

Glu Asp Leu Gly Asn Tyr Tyr Cys Leu Gln Tyr Ala Ala Ser Pro Phe
                85                  90                  95

Thr Phe Gly Ser Gly Thr Lys Leu Glu Ile Lys Arg Ala
            100                 105

(2) INFORMATION FOR SEQ ID NO:74:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Glu Leu Gln Met Thr Gln Thr Pro Ser Ser Leu Ser Val Ser Leu Gly
1               5                   10                  15

Glu Arg Val Ser Leu Thr Cys Arg Ala Ser Gln Asp Ile Gly Ser Ser
                20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Leu Val Asp Tyr Tyr Cys Leu Gln Tyr Ala Ser Ser Pro Trp
                85                  90                  95

Thr Phe Gly Gly Gly Thr Lys Leu Glu Ile Lys Arg Ala
            100                 105

(2) INFORMATION FOR SEQ ID NO:75:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Xaa Leu Gly Arg Gln Val Met Leu Ser Ser Lys Ala Ser Xaa Tyr Thr
1               5                   10                  15

Phe Thr Thr Tyr Gly Ile Ser Trp Val Lys Gln Arg Thr Gly Gln Gly
                20                  25                  30

Leu Glu Trp Ile Gly Glu Ile Cys Pro Arg Ser Gly Asn Thr Tyr Tyr
        35                  40                  45

Asn Glu Lys Phe Lys Gly Lys Ala Thr Leu Thr Ala Asp Lys Ser Ser
    50                  55                  60

Ser Thr Ala Tyr Leu Asp Leu Arg Ser Leu Thr Ser Glu Asp Ser Ala
65                  70                  75                  80

Val Tyr Phe Cys Ala Arg His Asp Gly Tyr Pro Phe Ala Tyr Trp Gly
                85                  90                  95
```

```
Gln Gly Thr Leu Val Thr Val Ser Ala
            100                 105
```

(2) INFORMATION FOR SEQ ID NO:76:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Leu Glu Gln Ser Gly Val Glu Leu Ala Arg Pro Gly Xaa Ser Val Lys
1               5                   10                  15

Leu Ser Cys Lys Ala Ser Gly Tyr Thr Phe Thr Thr Tyr Gly Ile Thr
            20                  25                  30

Trp Val Lys Gln Arg Thr Gly Gln Gly Leu Glu Trp Ile Gly Glu Ile
            35                  40                  45

Trp Pro Arg Ser Gly Asn Thr Tyr Tyr Asn Glu Lys Phe Lys Gly Lys
        50                  55                  60

Ala Thr Leu Thr Ala Asp Lys Ser Ser Thr Ala Tyr Met Glu Val
65                  70                  75                  80

Arg Ser Leu Thr Ser Asp Asp Ser Ala Val Tyr Phe Cys Ala Arg His
                85                  90                  95

Asp Gly Tyr Pro Phe Ala Tyr Trp Gly Gln Gly Thr Leu Val Thr Val
            100                 105                 110

Ser Ala
```

(2) INFORMATION FOR SEQ ID NO:77:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Leu Glu Gln Ser Gly Val Glu Leu Ala Gly Pro Gly Ala Ser Val Lys
1               5                   10                  15

Leu Ser Cys Lys Ala Ser Gly Tyr Thr Phe Thr Thr Tyr Gly Ile Ser
            20                  25                  30

Trp Val Lys Gln Arg Thr Gly Gln Gly Leu Glu Trp Ile Gly Glu Ile
            35                  40                  45

Trp Pro Arg Ser Gly Asn Thr Tyr Tyr Asn Glu Lys Phe Lys Gly Lys
        50                  55                  60

Ala Thr Leu Thr Ala Asp Lys Ser Ser Thr Ala Tyr Leu Asp Leu
65                  70                  75                  80

Arg Ser Leu Thr Ser Glu Asp Ser Ala Val Tyr Phe Cys Ala Arg His
                85                  90                  95

Asp Gly Tyr Pro Phe Ala Tyr Trp Gly Gln Gly Thr Leu Val Thr Val
            100                 105                 110

Ser Ala
```

(2) INFORMATION FOR SEQ ID NO:78:

```
        (i) SEQUENCE CHARACTERISTICS:
            (A) LENGTH: 91 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:78:

Xaa Thr Phe Thr Thr Tyr Gly Ile Thr Trp Val Lys Gln Arg Thr Gly
 1               5                  10                  15

Gln Gly Leu Glu Trp Ile Gly Glu Ile Trp Pro Arg Ser Gly Asn Thr
            20                  25                  30

Tyr Tyr Asn Glu Lys Phe Lys Gly Lys Ala Thr Leu Thr Ala Asp Lys
        35                  40                  45

Ser Ser Ser Thr Ala Tyr Met Glu Val Arg Ser Leu Thr Ser Asp Asp
50                  55                  60

Ser Ala Val Tyr Phe Cys Ala Arg His Asp Gly Tyr Pro Phe Ala Tyr
65                  70                  75                  80

Trp Gly Gln Gly Thr Leu Val Thr Val Ser Ala
                85                  90

(2) INFORMATION FOR SEQ ID NO:79:

(i) SEQUENCE CHARACTERISTICS:
            (A) LENGTH: 92 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:79:

Xaa Tyr Thr Phe Thr Thr Tyr Gly Ile Thr Trp Val Lys Gln Arg Thr
 1               5                  10                  15

Gly Gln Asp Leu Glu Trp Ile Gly Glu Ile Trp Pro Arg Ser Gly Asn
                20                  25                  30

Thr Tyr Tyr Asn Glu Lys Phe Lys Gly Lys Ala Thr Leu Ala Ala Asp
            35                  40                  45

Lys Ser Ser Ser Thr Ala Tyr Met Glu Leu Arg Ser Leu Thr Ser Asp
50                  55                  60

Asp Ser Ala Val Tyr Phe Cys Ala Arg His Asp Gly Tyr Pro Phe Ala
65                  70                  75                  80

Tyr Trp Asp Gln Gly Thr Leu Val Thr Val Ser Thr
                85                  90

(2) INFORMATION FOR SEQ ID NO:80:

(i) SEQUENCE CHARACTERISTICS:
            (A) LENGTH: 99 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:80:

Xaa Leu Ser Cys Lys Ala Ser Gly Tyr Thr Phe Thr Val Tyr Gly Ile
 1               5                  10                  15

Ser Trp Val Lys Gln Arg Thr Gly Gln Gly Leu Glu Trp Ile Gly Glu
                20                  25                  30

Ile Trp Pro Arg Ser Gly Asn Thr Tyr Tyr Asn Glu Lys Phe Lys Val
```

-continued

```
              35                  40                  45
Lys Ala Thr Leu Thr Ala Asp Lys Ser Ser Thr Ala Ser Met Glu
    50                  55                  60

Leu Arg Ser Leu Thr Ser Glu Asp Ser Ala Val Tyr Phe Cys Ala Arg
65                  70                  75                  80

His Asp Gly Tyr Pro Phe Ala Tyr Trp Gly Gln Gly Thr Leu Val Thr
                    85                  90                  95

Val Ser Ala
```

(2) INFORMATION FOR SEQ ID NO:81:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

```
Xaa Thr Phe Thr Val Tyr Gly Ile Ser Trp Val Lys Gln Arg Thr Gly
1               5                   10                  15

Gln Gly Leu Glu Trp Ile Gly Glu Ile Trp Pro Arg Ser Gly Asn Thr
                20                  25                  30

Tyr Tyr Asn Glu Lys Phe Lys Val Lys Ala Thr Leu Thr Xaa Asp Lys
                35                  40                  45

Ser Ser Ser Thr Ala Ser Met Glu Leu Arg Ser Leu Thr Ser Glu Asp
    50                  55                  60

Ser Ala Val Tyr Phe Cys Ala Arg His Asp Gly Tyr Pro Phe Ala Tyr
65                  70                  75                  80

Trp Gly Gln Gly Thr Leu Val Thr Val Ser Thr
                85                  90
```

(2) INFORMATION FOR SEQ ID NO:82:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
Ser Val Lys Leu Ser Cys Lys Ala Ser Gly Tyr Thr Phe Thr Thr Tyr
1               5                   10                  15

Gly Ile Ser Trp Val Lys Gln Arg Thr Gly Gln Gly Leu Glu Trp Ile
                20                  25                  30

Gly Glu Ile Trp Pro Arg Ser Gly Asn Thr Tyr Tyr Asn Glu Lys Phe
                35                  40                  45

Lys Gly Lys Ala Thr Leu Ser Ala Asp Lys Ser Ser Ser Thr Ala Tyr
    50                  55                  60

Leu Asp Leu Arg Ser Leu Thr Ser Glu Asp Ser Ala Val Tyr Phe Cys
65                  70                  75                  80

Ala Arg His Asp Gly Tyr Pro Phe Ala Tyr Trp Gly Gln Gly Thr Leu
                85                  90                  95

Val Thr Val Ser Ala
                100
```

-continued (2) INFORMATION FOR SEQ ID NO:83:

(i) SEQUENCE CHARACTERISTICS:
       (A) LENGTH: 108 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:83:

Glu Leu Xaa Xaa Pro Gly Ala Ser Val Lys Leu Ser Cys Lys Ala Ser
  1               5                  10                  15

Gly Xaa Thr Phe Thr Thr Tyr Gly Ile Thr Trp Val Lys Gln Arg Thr
             20                  25                  30

Gly Gln Gly Leu Glu Trp Ile Gly Glu Ile Trp Pro Arg Ser Gly Asn
         35                  40                  45

Thr Tyr Tyr Asn Glu Lys Phe Lys Gly Lys Ala Thr Leu Thr Ala Asp
     50                  55                  60

Lys Ser Ser Ser Thr Ala Tyr Met Glu Val Arg Ser Leu Thr Ser Asp
 65                  70                  75                  80

Asp Ser Ala Val Tyr Phe Cys Ala Arg His Asp Gly Tyr Pro Phe Ala
                 85                  90                  95

Tyr Trp Gly Gln Gly Thr Leu Val Thr Val Ser Ala
            100                 105

(2) INFORMATION FOR SEQ ID NO:84:

(i) SEQUENCE CHARACTERISTICS:
       (A) LENGTH: 103 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:84:

Pro Gly Pro Ser Val Lys Leu Ser Cys Lys Ala Ser Gly Tyr Thr Phe
  1               5                  10                  15

Thr Thr Tyr Gly Ile Ser Trp Val Lys Gln Arg Thr Gly Gln Gly Leu
             20                  25                  30

Glu Trp Ile Gly Glu Ile Trp Pro Arg Ser Gly Asn Thr Tyr Tyr Asn
         35                  40                  45

Glu Lys Phe Lys Gly Lys Ala Thr Leu Thr Ala Asp Lys Ser Ser Ser
     50                  55                  60

Thr Ala Tyr Leu Asp Leu Arg Ser Leu Thr Ser Glu Asp Ser Ala Val
 65                  70                  75                  80

Tyr Phe Cys Ala Arg His Asp Gly Tyr Pro Phe Ala Tyr Trp Gly Gln
                 85                  90                  95

Gly Thr Leu Val Thr Val Ser
            100

(2) INFORMATION FOR SEQ ID NO:85:

(i) SEQUENCE CHARACTERISTICS:
       (A) LENGTH: 92 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:85:

-continued

```
Xaa Asn Thr Phe Thr Thr Tyr Gly Ile Ser Trp Val Lys Gln Arg Thr
 1               5                  10                  15

Gly Gln Gly Leu Glu Trp Ile Gly Glu Ile Trp Pro Arg Ser Gly Asn
             20                  25                  30

Thr Tyr Tyr Asn Glu Lys Phe Lys Gly Lys Ala Thr Leu Thr Ala Asp
             35                  40                  45

Lys Ser Ser Ser Thr Ala Tyr Leu Asp Leu Arg Ser Leu Thr Ser Glu
     50                  55                  60

Asp Ser Ala Val Tyr Phe Cys Ala Arg His Asp Gly Tyr Pro Phe Ala
65                   70                  75                  80

Tyr Trp Gly Gln Gly Thr Leu Val Thr Val Ser Ala
                 85                  90
```

(2) INFORMATION FOR SEQ ID NO:86:

(i) SEQUENCE CHARACTERISTICS:
       (A) LENGTH: 95 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:86:

```
Xaa Ala Ser Gly Tyr Thr Phe Thr Thr Tyr Gly Ile Ser Trp Val Lys
 1               5                  10                  15

Gln Arg Thr Gly Gln Gly Leu Glu Trp Ile Gly Glu Ile Trp Pro Arg
             20                  25                  30

Ser Gly Asn Thr Tyr Tyr Asn Glu Lys Phe Lys Gly Lys Ala Thr Leu
             35                  40                  45

Thr Ala Asp Lys Ser Ser Ser Thr Ala Tyr Leu Asp Leu Arg Ser Leu
     50                  55                  60

Thr Ser Glu Asp Ser Ala Val Tyr Phe Cys Ala Arg His Asp Gly Tyr
65                   70                  75                  80

Pro Phe Ala Tyr Trp Gly Gln Gly Thr Leu Val Thr Val Ser Ala
                 85                  90                  95
```